United States Patent
Brady-Kalnay

(10) Patent No.: US 10,238,757 B2
(45) Date of Patent: *Mar. 26, 2019

(54) METHODS AND COMPOSITIONS FOR DETECTION OF CANCER

(71) Applicant: Case Western Reserve University, Cleveland, OH (US)

(72) Inventor: Susann Brady-Kalnay, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/188,404

(22) Filed: Feb. 24, 2014

(65) Prior Publication Data

US 2014/0178299 A1    Jun. 26, 2014

Related U.S. Application Data

(63) Continuation of application No. 13/059,025, filed as application No. PCT/US2009/053888 on Aug. 14, 2009, now Pat. No. 8,686,112.

(60) Provisional application No. 61/170,850, filed on Apr. 20, 2009, provisional application No. 61/088,955, filed on Aug. 14, 2008.

(51) Int. Cl.
| | |
|---|---|
| *A61K 49/00* | (2006.01) |
| *A61K 51/08* | (2006.01) |
| *G01N 33/574* | (2006.01) |
| *C07K 16/18* | (2006.01) |

(52) U.S. Cl.
CPC ...... *A61K 49/0058* (2013.01); *A61K 49/0032* (2013.01); *A61K 51/088* (2013.01); *C07K 16/18* (2013.01); *G01N 33/57407* (2013.01); *G01N 2333/70503* (2013.01)

(58) Field of Classification Search
CPC ............ A61K 39/0011; A61K 39/00; A61K 39/39558; A61K 2039/6031; A61K 2039/55516; A61K 2039/585; A61K 38/177; A61K 51/088; C12Q 1/6886; C07K 16/2863; C07K 16/40; C07K 14/4748

See application file for complete search history.

(56) References Cited

U.S. PATENT DOCUMENTS

| | | | |
|---|---|---|---|
| 8,686,112 B2 * | 4/2014 | Brady-Kalnay ... | A61K 49/0032 530/324 |
| 9,415,122 B2 * | 8/2016 | Brady-Kalnay ... | A61K 49/0058 |

FOREIGN PATENT DOCUMENTS

| | | | | |
|---|---|---|---|---|
| WO | WO2008024951 A1 * | 2/2008 | ............... | A61B 5/00 |

OTHER PUBLICATIONS

Fabre-Lafay et al. Nectin-4 is a new histological and serological tumor associated marker for breast cancer. BMC Cancer 2007, 7: 73. doi:10.1186/1471-2407-7-73. (Year: 2007).*

Fabre-Lafay et al. Nectin-4, a New Serological Breast Cancer Marker, Is a Substrate for Tumor Necrosis Factor-a-converting Enzyme (TACE)/ADAM-17. J. Biol. Chem. 2005, 280:19543-19550. (Year: 2005).*

* cited by examiner

*Primary Examiner* — Marcela M Cordero Garcia
*Assistant Examiner* — Jia-Hai Lee
(74) *Attorney, Agent, or Firm* — Tarolli, Sundheim, Covell & Tummino LLP

(57) ABSTRACT

A molecular probe for use in detection of cancer cells expressing an Ig superfamily cell adhesion molecule that binds in a homophilic fashion in a subject includes a targeting agent that specifically binds to and/or complexes with a proteolytically cleaved extracellular fragment of the Ig superfamily cell adhesion molecule.

16 Claims, 11 Drawing Sheets

Specification includes a Sequence Listing.

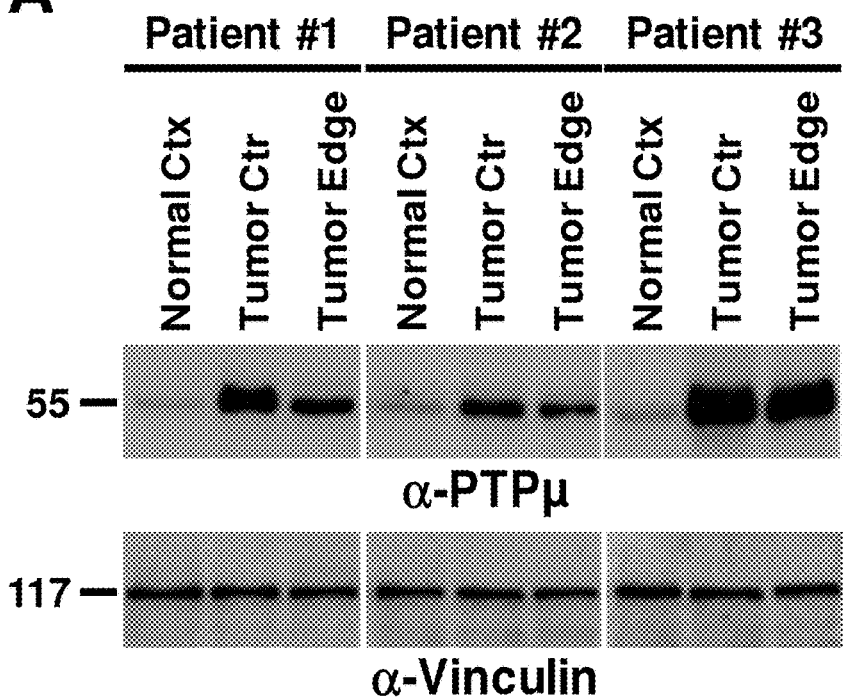
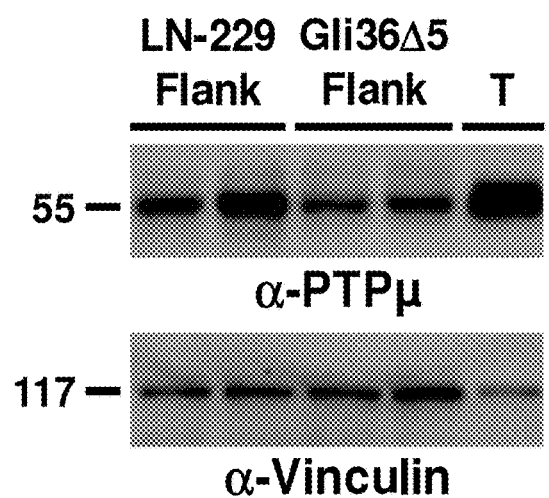
Fig. 1A-B

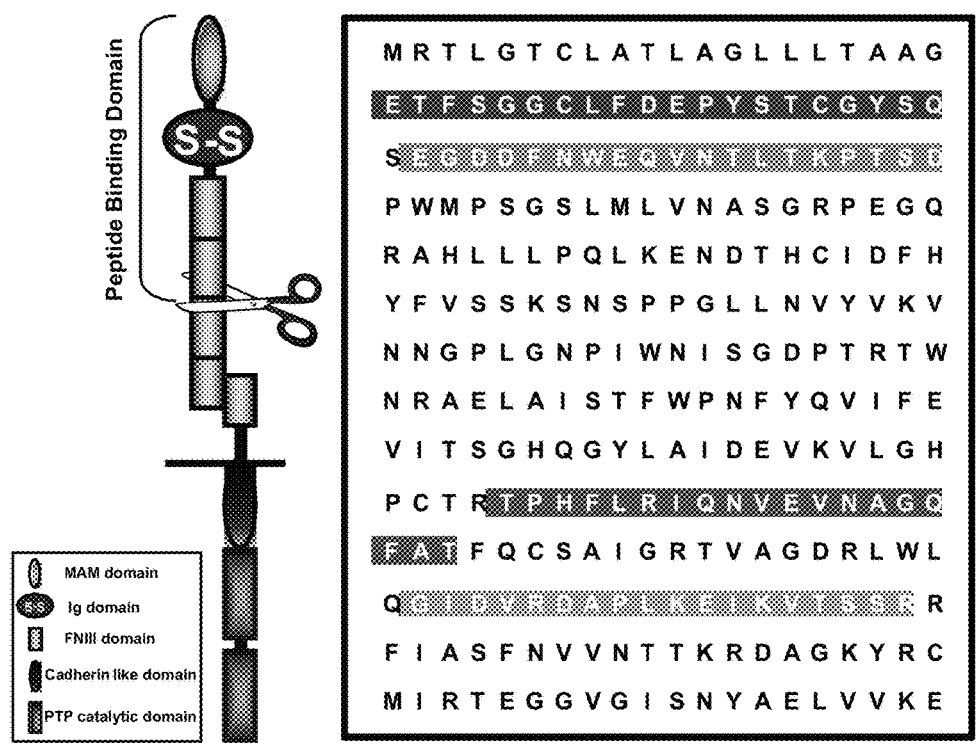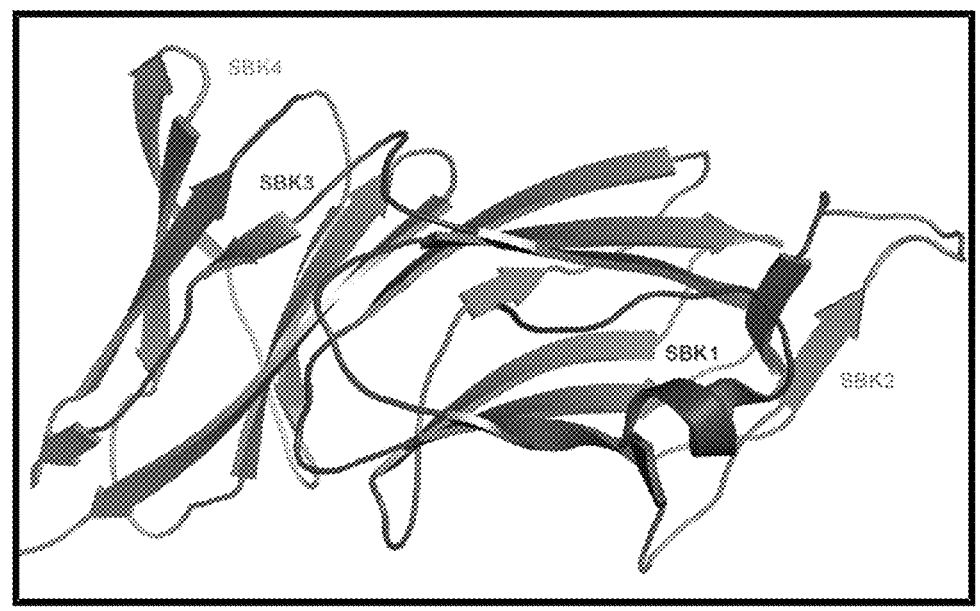
Fig. 2A-B

SEQUENCE LISTING

```
<160> NUMBER OF SEQ ID NOS: 7

<210> SEQ ID NO 1
<211> LENGTH: 1465
<212> TYPE: PRT
<213> ORGANISM: Homo sapiens

<400> SEQUENCE: 1

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
```

-continued

```
            115                 120                 125
Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                    165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                    195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
                260                 265                 270

Tyr Ala Glu Leu Val Val Lys Glu Pro Pro Val Pro Ile Ala Pro Pro
            275                 280                 285

Gln Leu Ala Ser Val Gly Ala Thr Tyr Leu Trp Ile Gln Leu Asn Ala
290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
            355                 360                 365

Ala Leu Arg Thr Arg Thr Lys Cys Ala Asp Pro Met Arg Gly Pro Arg
370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
                420                 425                 430

Val Ser Trp Asp Thr Glu Asn Ser His Pro Gln His Thr Ile Thr Asn
                435                 440                 445

Leu Ser Pro Tyr Thr Asn Val Ser Val Lys Leu Ile Leu Met Asn Pro
450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
                500                 505                 510

Ile Thr Leu Tyr Glu Ile Thr Tyr Lys Ala Val Ser Ser Phe Asp Pro
                515                 520                 525

Glu Ile Asp Leu Ser Asn Gln Ser Gly Arg Val Ser Lys Leu Gly Asn
530                 535                 540
```

```
Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
            580                 585                 590

Leu Glu Thr Pro Leu Asn Gln Thr Asp Asn Thr Val Thr Val Met Leu
        595                 600                 605

Lys Pro Ala His Ser Arg Gly Ala Pro Val Ser Val Tyr Gln Ile Val
610                 615                 620

Val Glu Glu Arg Pro Arg Thr Lys Thr Thr Glu Ile Leu
625                 630                 635                 640

Lys Cys Tyr Pro Val Pro Ile His Phe Gln Asn Ala Ser Leu Leu Asn
                645                 650                 655

Ser Gln Tyr Tyr Phe Ala Ala Glu Phe Pro Ala Asp Ser Leu Gln Ala
            660                 665                 670

Ala Gln Pro Phe Thr Ile Gly Asp Asn Lys Thr Tyr Asn Gly Tyr Trp
        675                 680                 685

Asn Thr Pro Leu Leu Pro Tyr Lys Ser Tyr Arg Ile Tyr Phe Gln Ala
    690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
                725                 730                 735

Thr Asp His Thr Val Lys Ile Ala Gly Val Ile Ala Gly Ile Leu Leu
            740                 745                 750

Phe Val Ile Ile Phe Leu Gly Val Val Leu Val Met Lys Lys Arg Lys
        755                 760                 765

Leu Ala Lys Lys Arg Lys Glu Thr Met Ser Ser Thr Arg Gln Glu Met
    770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
                805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Pro Phe Val Pro Thr
        835                 840                 845

Ala Ile Leu Val Pro Ile Asn Asp Glu Thr His Thr Met Ala Ser Asp
850                 855                 860

Thr Ser Ser Leu Val Gln Ser His Thr Tyr Lys Lys Arg Glu Pro Ala
865                 870                 875                 880

Asp Val Pro Tyr Gln Thr Gly Gln Leu His Pro Ala Ile Arg Val Ala
                885                 890                 895

Asp Leu Leu Gln His Ile Thr Gln Met Lys Cys Ala Glu Gly Tyr Gly
            900                 905                 910

Phe Lys Glu Glu Tyr Glu Ser Phe Phe Glu Gly Gln Ser Ala Pro Trp
        915                 920                 925

Asp Ser Ala Lys Lys Asp Glu Asn Arg Met Lys Asn Arg Tyr Gly Asn
    930                 935                 940

Ile Ile Ala Tyr Asp His Ser Arg Val Arg Leu Gln Thr Ile Glu Gly
945                 950                 955                 960
```

```
Asp Thr Asn Ser Asp Tyr Ile Asn Gly Asn Tyr Ile Asp Gly Tyr His
            965                 970                 975

Arg Pro Asn His Tyr Ile Ala Thr Gln Gly Pro Met Gln Glu Thr Ile
            980                 985                 990

Tyr Asp Phe Trp Arg Met Val Trp His Glu Asn Thr Ala Ser Ile Ile
            995                 1000                1005

Met Val Thr Asn Leu Val Glu Val Gly Arg Val Lys Cys Cys Lys
    1010                1015                1020

Tyr Trp Pro Asp Asp Thr Glu Ile Tyr Lys Asp Ile Lys Val Thr
    1025                1030                1035

Leu Ile Glu Thr Glu Leu Leu Ala Glu Tyr Val Ile Arg Thr Phe
    1040                1045                1050

Ala Val Glu Lys Arg Gly Val His Glu Ile Arg Glu Ile Arg Gln
    1055                1060                1065

Phe His Phe Thr Gly Trp Pro Asp His Gly Val Pro Tyr His Ala
    1070                1075                1080

Thr Gly Leu Leu Gly Phe Val Arg Gln Val Lys Ser Lys Ser Pro
    1085                1090                1095

Pro Ser Ala Gly Pro Leu Val Val His Cys Ser Ala Gly Ala Gly
    1100                1105                1110

Arg Thr Gly Cys Phe Ile Val Ile Asp Ile Met Leu Asp Met Ala
    1115                1120                1125

Glu Arg Glu Gly Val Val Asp Ile Tyr Asn Cys Val Arg Glu Leu
    1130                1135                1140

Arg Ser Arg Arg Val Asn Met Val Gln Thr Glu Glu Gln Tyr Val
    1145                1150                1155

Phe Ile His Asp Ala Ile Leu Glu Ala Cys Leu Cys Gly Asp Thr
    1160                1165                1170

Ser Val Pro Ala Ser Gln Val Arg Ser Leu Tyr Tyr Asp Met Asn
    1175                1180                1185

Lys Leu Asp Pro Gln Thr Asn Ser Ser Gln Ile Lys Glu Glu Phe
    1190                1195                1200

Arg Thr Leu Asn Met Val Thr Pro Thr Leu Arg Val Glu Asp Cys
    1205                1210                1215

Ser Ile Ala Leu Leu Pro Arg Asn His Glu Lys Asn Arg Cys Met
    1220                1225                1230

Asp Ile Leu Pro Pro Asp Arg Cys Leu Pro Phe Leu Ile Thr Ile
    1235                1240                1245

Asp Gly Glu Ser Ser Asn Tyr Ile Asn Ala Ala Leu Met Asp Ser
    1250                1255                1260

Tyr Lys Gln Pro Ser Ala Phe Ile Val Thr Gln His Pro Leu Pro
    1265                1270                1275

Asn Thr Val Lys Asp Phe Trp Arg Leu Val Leu Asp Tyr His Cys
    1280                1285                1290

Thr Ser Val Val Met Leu Asn Asp Val Asp Pro Ala Gln Leu Cys
    1295                1300                1305

Pro Gln Tyr Trp Leu Glu Asn Gly Val His Arg His Gly Pro Ile
    1310                1315                1320

Gln Val Glu Phe Val Ser Ala Asp Leu Glu Glu Asp Ile Ile Ser
    1325                1330                1335

Arg Ile Phe Arg Ile Tyr Asn Ala Ala Arg Pro Gln Asp Gly Tyr
    1340                1345                1350

Arg Met Val Gln Gln Phe Gln Phe Leu Gly Trp Pro Met Tyr Arg
```

```
                    1355                1360                1365
Asp  Thr  Pro  Val  Ser  Lys  Arg  Ser  Phe  Leu  Lys  Leu  Ile  Arg  Gln
               1370                1375                1380

Val  Asp  Lys  Trp  Gln  Glu  Glu  Tyr  Asn  Gly  Gly  Glu  Gly  Arg  Thr
1385                1390                1395

Val  Val  His  Cys  Leu  Asn  Gly  Gly  Gly  Arg  Ser  Gly  Thr  Phe  Cys
     1400                1405                1410

Ala  Ile  Ser  Ile  Val  Cys  Glu  Met  Leu  Arg  His  Gln  Arg  Thr  Val
          1415                1420                1425

Asp  Val  Phe  His  Ala  Val  Lys  Thr  Leu  Arg  Asn  Asn  Lys  Pro  Asn
               1430                1435                1440

Met  Val  Asp  Leu  Leu  Asp  Gln  Tyr  Lys  Phe  Cys  Tyr  Glu  Val  Ala
1445                1450                1455

Leu  Glu  Tyr  Leu  Asn  Ser  Gly
          1460                1465

<210> SEQ ID NO 2
<211> LENGTH: 477
<212> TYPE: PRT
<213> ORGANISM: Homo sapiens

<400> SEQUENCE: 2

Met  Arg  Gly  Leu  Gly  Thr  Cys  Leu  Ala  Thr  Leu  Ala  Gly  Leu  Leu
1                   5                   10                  15

Thr  Ala  Ala  Gly  Glu  Thr  Phe  Ser  Gly  Gly  Cys  Leu  Phe  Asp  Glu  Pro
               20                  25                  30

Tyr  Ser  Thr  Cys  Gly  Tyr  Ser  Gln  Ser  Glu  Gly  Asp  Asp  Phe  Asn  Trp
          35                  40                  45

Glu  Gln  Val  Asn  Thr  Leu  Thr  Lys  Pro  Thr  Ser  Asp  Pro  Trp  Met  Pro
50                  55                  60

Ser  Gly  Ser  Phe  Met  Leu  Val  Asn  Ala  Ser  Gly  Arg  Pro  Glu  Gly  Gln
65                  70                  75                  80

Arg  Ala  His  Leu  Leu  Leu  Pro  Gln  Leu  Lys  Glu  Asn  Asp  Thr  His  Cys
               85                  90                  95

Ile  Asp  Phe  His  Tyr  Phe  Val  Ser  Lys  Ser  Asn  Ser  Pro  Pro  Gly
               100                 105                 110

Leu  Leu  Asn  Val  Tyr  Val  Lys  Val  Asn  Asn  Gly  Pro  Leu  Gly  Asn  Pro
          115                 120                 125

Ile  Trp  Asn  Ile  Ser  Gly  Asp  Pro  Thr  Arg  Thr  Trp  Asn  Arg  Ala  Glu
130                 135                 140

Leu  Ala  Ile  Ser  Thr  Phe  Trp  Pro  Asn  Phe  Tyr  Gln  Val  Ile  Phe  Glu
145                 150                 155                 160

Val  Ile  Thr  Ser  Gly  His  Gln  Gly  Tyr  Leu  Ala  Ile  Asp  Glu  Val  Lys
               165                 170                 175

Val  Leu  Gly  His  Pro  Cys  Thr  Arg  Thr  Pro  His  Phe  Leu  Arg  Ile  Gln
          180                 185                 190

Asn  Val  Glu  Val  Asn  Ala  Gly  Gln  Phe  Ala  Thr  Phe  Gln  Cys  Ser  Ala
          195                 200                 205

Ile  Gly  Arg  Thr  Val  Ala  Gly  Asp  Arg  Leu  Trp  Leu  Gln  Gly  Ile  Asp
          210                 215                 220

Val  Arg  Asp  Ala  Pro  Leu  Lys  Glu  Ile  Lys  Val  Thr  Ser  Ser  Arg  Arg
225                 230                 235                 240

Phe  Ile  Ala  Ser  Phe  Asn  Val  Val  Asn  Thr  Thr  Lys  Arg  Asp  Ala  Gly
               245                 250                 255
```

```
Lys Tyr Arg Cys Met Ile Arg Thr Glu Gly Val Gly Ile Ser Asn
                260                 265                 270
Tyr Ala Glu Leu Val Val Lys Glu Pro Pro Val Pro Ile Ala Pro Pro
        275                 280                 285
Gln Leu Ala Ser Val Gly Ala Thr Tyr Leu Trp Ile Gln Leu Asn Ala
290                 295                 300
Asn Ser Ile Asn Gly Asp Gly Pro Ile Val Ala Arg Glu Val Glu Tyr
305                 310                 315                 320
Cys Thr Ala Ser Gly Ser Trp Asn Asp Arg Gln Pro Val Asp Ser Thr
                325                 330                 335
Ser Tyr Lys Ile Gly His Leu Asp Pro Asp Thr Glu Tyr Glu Ile Ser
                340                 345                 350
Val Leu Leu Thr Arg Pro Gly Glu Gly Gly Thr Gly Ser Pro Gly Pro
                355                 360                 365
Ala Leu Arg Thr Arg Thr Lys Cys Ala Asp Pro Met Arg Gly Pro Arg
                370                 375                 380
Lys Leu Glu Val Val Glu Val Lys Ser Arg Gln Ile Thr Ile Arg Trp
385                 390                 395                 400
Glu Pro Phe Gly Tyr Asn Val Thr Arg Cys His Ser Tyr Asn Leu Thr
                405                 410                 415
Val His Tyr Cys Tyr Gln Val Gly Gly Gln Glu Gln Val Arg Glu Glu
                420                 425                 430
Val Ser Trp Asp Thr Glu Asn Ser His Pro Gln His Thr Ile Thr Asn
                435                 440                 445
Leu Ser Pro Tyr Thr Asn Val Ser Val Lys Leu Ile Leu Met Asn Pro
                450                 455                 460
Glu Gly Arg Lys Glu Ser Gln Glu Leu Ile Val Gln Thr
465                 470                 475

<210> SEQ ID NO 3
<211> LENGTH: 280
<212> TYPE: PRT
<213> ORGANISM: Homo sapiens

<400> SEQUENCE: 3

Met Arg Gly Leu Gly Thr Cys Leu Ala Thr Leu Ala Gly Leu Leu Leu
1               5                   10                  15
Thr Ala Ala Gly Glu Thr Phe Ser Gly Gly Cys Leu Phe Asp Glu Pro
                20                  25                  30
Tyr Ser Thr Cys Gly Tyr Ser Gln Ser Glu Gly Asp Asp Phe Asn Trp
            35                  40                  45
Glu Gln Val Asn Thr Leu Thr Lys Pro Thr Ser Asp Pro Trp Met Pro
50              55                  60
Ser Gly Ser Phe Met Leu Val Asn Ala Ser Gly Arg Pro Glu Gly Gln
65                  70                  75                  80
Arg Ala His Leu Leu Leu Pro Gln Leu Lys Glu Asn Asp Thr His Cys
                85                  90                  95
Ile Asp Phe His Tyr Phe Val Ser Ser Lys Ser Asn Ser Pro Pro Gly
            100                 105                 110
Leu Leu Asn Val Tyr Val Lys Val Asn Asn Gly Pro Leu Gly Asn Pro
        115                 120                 125
Ile Trp Asn Ile Ser Gly Asp Pro Thr Arg Thr Trp Asn Arg Ala Glu
130                 135                 140
Leu Ala Ile Ser Thr Phe Trp Pro Asn Phe Tyr Gln Val Ile Phe Glu
145                 150                 155                 160
```

```
Val Ile Thr Ser Gly His Gln Gly Tyr Leu Ala Ile Asp Glu Val Lys
            165                 170                 175

Val Leu Gly His Pro Cys Thr Arg Thr Pro His Phe Leu Arg Ile Gln
        180                 185                 190

Asn Val Glu Val Asn Ala Gly Gln Phe Ala Thr Phe Gln Cys Ser Ala
    195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
            245                 250                 255

Lys Tyr Arg Cys Met Ile Arg Thr Glu Gly Gly Val Gly Ile Ser Asn
        260                 265                 270

Tyr Ala Glu Leu Val Val Lys Glu
    275                 280

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Glu Thr Phe Ser Gly Gly Cys Leu Phe Asp Glu Pro Tyr Ser Thr Cys
1               5                   10                  15

Gly Tyr Ser Gln
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Glu Gly Asp Asp Phe Asn Trp Glu Gln Val Asn Thr Leu Thr Lys Pro
1               5                   10                  15

Thr Ser Asp

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Thr Pro His Phe Leu Arg Ile Gln Asn Val Glu Val Asn Ala Gly Gln
1               5                   10                  15

Phe Ala Thr

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 7

Gly Ile Asp Val Arg Asp Ala Pro Leu Lys Glu Ile Lys Val Thr Ser
1               5                   10                  15

Ser Arg
```

METHODS AND COMPOSITIONS FOR DETECTION OF CANCER

RELATED APPLICATION

This application claims priority from U.S. Provisional Application Nos. 60/088,955, filed Aug. 14, 2008 and 61/170,850 filed Apr. 20, 2009, the subject matter of which are incorporated herein by reference in their entirety.

GOVERNMENT FUNDING

This invention was made with government support under Grant No. NS051520 awarded by The National Institutes of Health. The United States government has certain rights in the invention.

BACKGROUND

The prognosis for high-grade brain tumors, such as glioblastoma multiforme (GBM) is extremely poor with a median survival of about one year from diagnosis (Ichimura K, Ohgaki H, Kleihues P, Collins V P (2004) Molecular pathogenesis of astrocytic tumours. J Neurooncol 70:137-160; Louis D N, Ohgaki H, Wiestler O D, Cavenee W K (2007) World Health Organization Classification of Tumours of the Nervous System, 4th Edition. Lyon: IARC). Several biological characteristics contribute to the lethality of GBM tumors, including their uncontrolled proliferation in the restricted cranial space, and their highly dispersive nature (Ichimura K, Ohgaki H, Kleihues P, Collins V P (2004) Molecular pathogenesis of astrocytic tumours. J Neurooncol 70:137-160; Louis D N, Ohgaki H, Wiestler O D, Cavenee W K (2007) World Health Organization Classification of Tumours of the Nervous System, 4th Edition. Lyon: IARC; Louis D N (2006) Molecular pathology of malignant gliomas. Annu Rev Pathol 1:97-117). Surgical resection remains the primary treatment for glial tumors (Furnari F B, Fenton T, Bachoo R M, Mukasa A, Stommel J M, Stegh A, Hahn W C, Ligon K L, Louis D N, Brennan C, Chin L, DePinho R A, Cavenee W K (2007) Malignant astrocytic glioma: genetics, biology, and paths to treatment. Genes Dev 21:2683-2710) and more complete resection has been linked to improved survival (Sanai N, Berger M S (2008) Glioma extent of resection and its impact on patient outcome. Neurosurgery 62:753-764; discussion 264-756). However, by the time of diagnosis, GBM cells have usually dispersed extensively into the surrounding brain, making it difficult for the surgeon to precisely localize the tumor margin (Nakada M, Nakada S, Demuth T, Tran N L, Hoelzinger D B, Berens M E (2007) Molecular targets of glioma invasion. Cell Mol Life Sci 64:458-478). Magnetic resonance imaging (MRI) guided stereotactic techniques are typically utilized to maximize resection. However, MRI is limited in its ability to detect sparse tumor cells invading surrounding normal brain (Sorensen A G, Batchelor T T, Wen P Y, Zhang W T, Jain R K (2008) Response criteria for glioma. Nat Clin Pract Oncol 5:634-644). Since nearly all glioblastomas recur locally, better detection would likely improve surgical resection resulting in enhanced patient survival.

SUMMARY

The present invention relates to a molecular probe for use in detection of cancer cells expressing an immunoglobulin (Ig) superfamily cell adhesion molecule that includes an extracellular homophilic binding portion, which can bind in homophilic fashion or engage in homophilic binding in a subject. The molecular probe includes a targeting agent that specifically binds to and/or complexes with a proteolytically cleaved extracellular fragment of the Ig superfamily cell adhesion molecule.

In one aspect of the invention, the Ig superfamily cell adhesion molecule can include a cell surface receptor protein tyrosine phosphatase (PTP) type IIb, such as PTPµ or a PTPµ like molecule. The cancer cell can be a glioma cell and, specifically, a glioblastoma multiforme (GBM) cell.

In another aspect of the invention, the extracellular fragment can have an amino acid sequence of SEQ ID NO: 2. The targeting agent can specifically bind to and/or complex with SEQ ID NO: 2. In a further aspect, the targeting agent can bind to homophilic binding domains or portion of the extracellular fragment, such as SEQ ID NO: 3, which comprises the MAM, Ig and first two FNIII repeat binding domain of PTPµ.

In yet another aspect of the invention, the targeting agent can include a peptide having an amino acid sequence that is substantially homologous to about 10 to about 50 consecutive amino acids of the amino acid sequence of SEQ ID NO: 3. Examples of peptides having an amino acid sequence substantially homologous to SEQ ID NO: 3 can be peptides having an amino acid sequence selected from the group consisting of SEQ ID NO: 4, SEQ ID NO: 5, SEQ ID NO: 6, and SEQ ID NO: 7.

In another aspect of the invention, the molecular probe can include a detectable moiety that is linked to the targeting agent. The molecular probe can be detected in vivo by recognizing the detectable moiety. The detectable moiety can be detected by at least one of gamma imaging, positron emission tomography (PET) imaging, computer tomography (CT) imaging, magnetic resonance imaging, near infrared imaging, or fluorescent imaging.

The present invention also relates to a method of detecting cancer cells expressing an Ig superfamily cell adhesion molecule that binds in a homophilic fashion in a subject. The method includes administering a molecular probe to the subject. The molecular probe can include a targeting agent that specifically binds to and/or complexes with a proteolytically cleaved extracellular fragment of the Ig superfamily cell adhesion molecule and imaging agent linked to the targeting agent. The molecular probe bound to and/or complexed with the proteolytically cleaved extracellular fragment of the Ig superfamily cell adhesion molecule is detected in the subject to provide the location and/or distribution of the cancer cells in the subject.

In an aspect of the invention, the Ig superfamily cell adhesion molecule can include a cell surface receptor protein tyrosine phosphatase (PTP) type IIb, such as PTPµ or a PTPµ like molecule. The cancer cell can be a glioma cell and, specifically, a glioblastoma multiforme (GBM) cell.

In another aspect of the invention, the extracellular fragment can have an amino acid sequence of SEQ ID NO: 2. The targeting agent can specifically bind to and/or complex with SEQ ID NO: 2. In a further aspect, the targeting agent can bind to homophilic binding domains or portion of the extracellular fragment, such as SEQ ID NO: 3, which comprises the MAM and Ig binding domain of PTPµ.

In yet another aspect of the invention, the targeting agent can include a peptide having an amino acid sequence that is substantially homologous to about 10 to about 50 consecutive amino acids of the amino acid sequence of SEQ ID NO: 3. Examples of peptides having an amino acid sequence substantially homologous to SEQ ID NO: 3 can be peptides having an amino acid sequence selected from the group consisting of SEQ ID NO: 4, SEQ ID NO: 5, SEQ ID NO: 6, and SEQ ID NO: 7.

The molecular probe can detected in vivo by detecting the detectable moiety. The detectable moiety can be detected by at least one of gamma imaging, positron emission tomography (PET) imaging, computer tomography (CT) imaging, magnetic resonance imaging, near infrared imaging, or fluorescent imaging.

BRIEF DESCRIPTION OF THE DRAWINGS

FIG. 1 illustrates a series of immunoblots showing a 55 kDa extracellular fragment of PTPµ is detected in human glioblastoma tissue. (A) GBM tumors from three patients were divided into center (ctr) and edge samples, lysed, separated by SDS-PAGE and immunoblotted using an antibody against the MAM domain of PTPµ. Noncancerous normal cortex (ctx) from the same patients was loaded for comparison. Equal protein load was verified by stripping and reprobing the immunoblot with an antibody to vinculin. (B) LN-229 or Gli36Δ5 xenograft flank tumor protein extracts were immunoblotted as above. Human GBM tumor tissue (T) was loaded on the same blot for comparison.

FIG. 2 is a schematic illustration of a PTPµ structure and targeting peptide probe sequences. PTPµ is a transmembrane protein that mediates efficient cell-cell adhesion via the MAM domain, Ig domain and FNIII repeats within its extracellular segments. (A) The scissors indicate the approximate site where PTPµ is cleaved to generate a 55 kDa N-terminal fragment. The sequence is shown for the PTPµ MAM and Ig domains (i.e., SEQ ID NO: 2). The highlighted regions indicate the sequences used to generate PTPµ peptide probes (i.e., SBK1 (SEQ ID NO: 4), SBK2 (SEQ ID NO: 5), SBK3 (SEQ ID NO: 6), and SBK4 (SEQ ID NO: 7). (B) Crystal structure of the Ig and MAM domains of PTPµ (PDB ID:2V5Y). SBK1 (SEQ ID NO: 4) and SBK2 (SEQ ID NO: 5) were derived from the N-terminal MAM domain while SBK3 (SEQ ID NO: 6) and SBK4 (SEQ ID NO: 7) were from the Ig domain.

DETAILED DESCRIPTION

Figure 3:
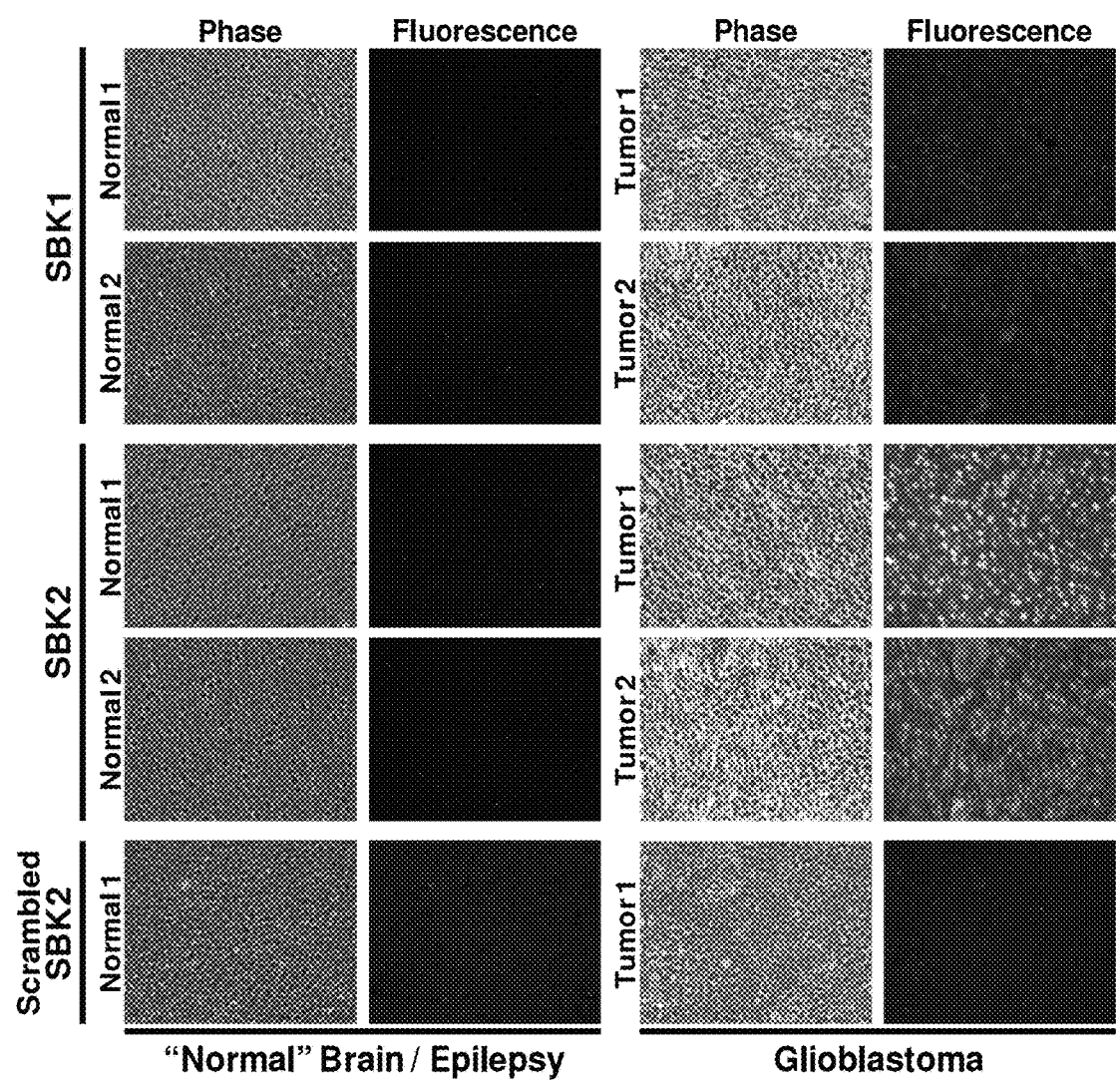
FIG. 3 illustrates images showing SBK2 peptide (SEQ ID NO: 5) probe specifically recognizes human glioblastoma tissue but not normal brain. Sections of noncancerous normal cortical brain tissue from epilepsy patients or GBM tumor were histochemically labeled with Texas Red-conjugated SBK1 (SEQ ID NO: 4), SBK2 (SEQ ID NO: 5) or Scrambled SBK2 peptide. Two examples of normal and GBM tissue are shown that are representative of 6 different samples examined.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "monoclonal" refers to an antibody that specifically binds to a sequence of amino acid and/or a specific epitope of an antigen.

The term "polyclonal" refers to an antibody that recognizes multiple epitope sites on a single antigen.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The term "agent" is used herein to denote a chemical compound, a mixture of chemical compounds, a biological macromolecule, or an extract made from biological materials.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The present invention relates to a molecular probe for use in detection of cancer cells expressing an Ig superfamily cell adhesion molecule that includes an extracellular homophilic binding portion or segment, which binds in a homophilic fashion or engages in homophilic binding in a subject. The molecular probe of the present invention can be administered systemically to a subject and readily cross the blood brain barrier to define cancer metastases or tumor cell margin in the subject.

It was found that metastic cancer cell migration or cancer cell dispersal, such as glioblastoma multiforme (GBM) cell dispersal, can occur along characteristic pathways of anatomical structures (e.g., brain), which are rich in cell adhesion molecules (CAMs) and extracellular matrix molecules (ECM) that are permissive substrates for cell migration. In some instances, cancer cell dispersal, such as GBM cell dispersal, requires the production of proteolytic enzymes, which gives the cell the ability to move through its environment. For example, GBM cells overexpress growth factor receptor protein tyrosine kinases and their ligands, which is an important prerequisite for tumor growth and dispersal. The activity of the receptor tyrosine kinases is normally kept in check by the opposing activity of protein tyrosine phosphatases, such as receptor protein tyrosine phosphatases (RPTPs) (e.g., PTPμ), which are thought to be important regulators of adhesion-dependent signals. Receptor protein tyrosine phosphatases, such as RPTP type IIb cell adhesion molecules, have been shown to regulate neural development and axon guidance. Ensslen-Craig S E, Brady-Kalnay S M (2004) Receptor protein tyrosine phosphatases regulate neural development and axon guidance. Dev Biol 275:12-22; Tonks N K (2006) Protein tyrosine phosphatases: from genes, to function, to disease. Nat Rev Mol Cell Biol 7:833-846).

RPTP type IIb cell adhesion molecules can include an extracellular segment that engages in homophilic binding. For example, the extracellular fragment of PTPμ, which is expressed by GBM cells, can include a MAM domain, an immunoglobulin (Ig) domain and four fibronectin type III (FNIII) repeats. PTPμ binds homophilically (i.e., the "ligand" for PTPμ is an identical PTPμ molecule on an adjacent cell) and can mediate cell-cell aggregation. The Ig domain of PTPμ is responsible for promoting homophilic interactions and proper cell surface localization. The MAM domain also plays an important role in cell adhesion and sorting. The first two FNIII repeats contribute to efficient cell adhesion. When expressed on the cell surface, PTPμ mediates cell-cell adhesion and transduces signals in response to adhesion that may regulate contact inhibition of movement.

In at least some human cancer cells that express Ig superfamily cell adhesion molecules that include an extracellular segment, which engages in homophilic binding, (e.g., PTPμ) the extracellular fragment is proteolytically cleaved and found to associate with or localize to the cancer cell margin or surface. It was found that molecular probes, that can specifically bind to and/or complex with these proteolytically cleaved extracellular fragments or segments can be used to detect can cancer cell migration, tumor cell dispersal, tumor cell invasion and define cancer metastases and tumor margins in a subject.

By way of example, it was determined that proteolytically cleaved PTPμ extracellular fragments are common to highgrade glioblastomas. Molecular probes to the PTPμ fragment were shown to clearly demarcate the tumor cells in tissue sections and the PTPμ extracellular fragment is present in human tumor "edge" samples, suggesting that the molecular probe can be used as diagnostic tools for molecular imaging of dispersive brain tumors or the tumor margin. Systemic introduction of molecular probes in accordance with the present invention resulted in rapid and specific labeling of the flank tumors within minutes. Labeling occurred primarily within the tumor, however a gradient of molecular probe at the tumor margin was also observed.

One aspect of the present invention therefore relates to a method of detecting cancer cells expressing an Ig superfamily cell adhesion molecule that binds in a homophilic fashion in a subject by detecting a proteolytically cleaved extracellular fragment of the Ig superfamily cell adhesion molecule with a molecular probe. In one example, the Ig superfamily cell adhesion molecule that engages in homophilic binding can include RPTP type IIb cell adhesion molecules. In another example, Ig superfamily cell adhesion molecules that engage in homophilic binding can include RPTPs of the PTPμ-like subfamily, such as PTPμ, PTPκ, PTPρ, and PCP-2 (also called PTPλ).

PTPμ-like RPTPs include a MAM (Meprin/A5-protein/PTPμ) domain, an Ig domain, and FNIII repeats. PTPμ can have the amino acid sequence of SEQ ID NO: 1, which is identified by Genbank Accession No. AAI51843.1. It will be appreciated that the PTPμ gene can generate splice variants such that the amino acid sequence of PTPμ can differ from SEQ ID NO: 1. In some embodiments of the invention, PTPμ can have an amino acid sequence identified by Genbank Accession No. AAH51651.1 and Genbank Accession No. AAH40543.1.

Cancer cells that express an Ig superfamily cell adhesion molecule that binds in a homophilic fashion and that can be proteolytically cleaved to produce a detectable extracellular fragment can include, for example, metastic or motile cancer cells. In one example, the invasive, dispersive, motile or metastic cancer cells can include glioma cells. The term glioma, as used herein, refers to a type of cancer arising from glial cells in the brain or spine. Gliomas as contemplated by the present invention can be classified by cell type, by tumor grade, and/or by location. For example, ependymomas resemble ependymal cells, astrocytomas (e.g. glioblastoma multiforme) resemble astrocytes, oligodedrogliomas resemble oligodendrocytes. Also mixed gliomas, such as oligoastrocytomas may contain cells from different types of glia. Gliomas can also be classified according to whether they are above or below a membrane in the brain called the tentorium. The tentorium separates the cerebrum, above, from the cerebellum, below. A supratentorial glioma is located above the tentorium, in the cerebrum, and occurs mostly in adults whereas an infratentorial glioma is located below the tentorium, in the cerebellum, and occurs mostly in children. Other examples of cancer cells that express an Ig superfamily cell adhesion molecule that binds in a homophilic fashion can be readily determined by using, for example, immunoassays.

The molecular probe that is used to detect the extracellular fragment of the proteolytically cleaved extracellular fragment of the Ig superfamily cell adhesion molecule that engages in homophilic binding can include a targeting agent that specifically binds to and/or complexes with the proteolytically cleaved extracellular fragment of the Ig superfamily cell adhesion molecule of the cancer cell. The targeting agent can include a targeting small molecule, peptide, or antibody that binds to and/or complexes with the proteolytically cleaved extracellular fragment of the Ig superfamily cell adhesion molecule and that can readily be administered to the subject using, for example, parenteral or systemic administration techniques (e.g., intravenous infusion).

In one aspect of the invention, the targeting agent can include a peptide or targeting peptide that binds to and/or complexes with the proteolytically cleaved extracellular fragment of the Ig superfamily cell adhesion molecule. The targeting peptide can have an amino acid sequence that is substantially homologous to about 10 to about 50 consecutive amino acids of a homophilic binding portion or domain of the proteleolytically cleaved extracellular fragment of the Ig superfamily cell adhesion molecule. By substantially homologous, it is meant the targeting peptide has at least about 80%, about 90%, about 95%, about 96%, about 97%, about 98%, about 99% or about 100% sequence identity with a portion of the amino acid sequence of the homophilic binding portion of the proteleolytically cleaved extracellular fragment of the Ig superfamily cell adhesion molecule.

In one example, the homophilic binding portion of the Ig superfamily cell adhesion molecule can include, for example, the Ig domain of the cell adhesion molecule. In another example, where the Ig superfamily cell adhesion molecule is PTPµ, the homophilic binding portion can include the Ig binding domain and the MAM domain.

In another aspect of the invention, the targeting peptide can have an amino acid sequence that is substantially homologous to about 10 to about 50 consecutive amino acids of the Ig binding domain and/or MAM domain of PTPµ (e.g., SEQ ID NO: 1) and readily cross the blood brain barrier when systemically administered to a subject. The development of the PTPµ targeting peptides can be based on a large body of structural and functional data. The sites required for PTPµ-mediated homophilic adhesion have been well characterized. In addition, the crystal structure of PTPµ can provide information regarding which regions of each functional domain are likely to be exposed to the outside environment and therefore available for homophilic binding and thus detection by a peptide probe.

In yet another aspect of the invention, the proteolytically cleaved extracellular fragment of PTPµ (e.g., SEQ ID NO: 1) can include an amino acid sequence of SEQ ID NO: 2, the Ig and MAM binding region can comprise the amino acid sequence of SEQ ID NO: 3, and targeting peptide can have an amino acid sequence that is substantially homologous to about 10 to about 50 consecutive amino acids of SEQ ID NO: 2 or SEQ ID NO: 3. Examples of targeting peptide that can specifically bind SEQ ID NO: 2 or SEQ ID NO: 3 can have an amino acid sequence selected from the group consisting of SEQ ID NO: 4, SEQ ID NO:5, SEQ ID NO: 6, and SEQ ID NO: 7. Targeting peptides comprising SEQ ID NO: 4 or 5 can recognize or bind to the MAM domain; whereas targeting peptides comprising SEQ ID NO: 6 or 7 can recognize or bind to the Ig domain. Targeting peptides comprising SEQ ID NO: 4, 5, 6 or 7 can recognize or bind to the MAM, Ig domain or the FNIII repeats.

The targeting peptides in accordance with the present invention can be subject to various changes, substitutions, insertions, and deletions where such changes provide for certain advantages in its use. In this regard, targeting peptides that binds to and/or complex with a proteolytically cleaved extracellular portion of an Ig superfamily cell adhesion molecule can correspond to or be substantially homologous with, rather than be identical to, the sequence of a recited peptide where one or more changes are made and it retains the ability to function as specifically binding to and/or complexing with the proteolytically cleaved extracellular portion of an Ig superfamily cell adhesion molecule.

The targeting peptide can be in any of a variety of forms of peptide derivatives, that include amides, conjugates with proteins, cyclized peptides, polymerized peptides, analogs, fragments, chemically modified peptides, and the like derivatives.

The term "analog" includes any peptide having an amino acid residue sequence substantially identical to a sequence specifically shown herein in which one or more residues have been conservatively substituted with a functionally similar residue and that specifically binds to and/or complexes with the proteolytically cleaved extracellular portion of an Ig superfamily cell adhesion molecule as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions and/or deletions or residues relative to the sequence of a peptide whose sequence is shown herein, so long as the requisite activity is maintained.

The term "fragment" refers to any subject peptide having an amino acid residue sequence shorter than that of a peptide whose amino acid residue sequence is shown herein.

Additional residues may also be added at either terminus of a peptide for the purpose of providing a "linker" by which the peptides of this invention can be conveniently affixed to a detectable moiety, label, solid matrix, or carrier.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide or compound of the present invention may also be used in the form of a pharmaceutically acceptable salt. Acids, which are capable of forming salts with the peptides of the present invention, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the peptides of the present invention include inorganic bases such as sodium hydroxide, ammonium hydroxide, potassium hydroxide and the like; and organic bases such as mono-, di- and tri-alkyl and aryl-amines (e.g., triethylamine, diisopropylamine, methylamine, dimethylamine and the like) and optionally substituted ethanolamines (e.g. ethanolamine, diethanolamine and the like).

Targeting peptides of the present invention can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (N.Y.), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (N.Y.), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

It will be appreciated that the targeting peptide can bind to and/or complex with homophilic binding domains of proteolytically cleaved extracellular fragments of other Ig superfamily cell adhesion molecules, besides PTPs. For example, a similar molecular detection strategy described herein can be used with any other Ig superfamily cell adhesion molecule having a homophilic binding cell surface protein whose ligand binding site is known. A large variety of cell surface proteins, including other phosphatases, are cleaved at the cell surface (Streuli M, Krueger N, Ariniello P, Tang M, Munro J, Blattler W, Adler D, Disteche C, Saito H (1992) Expression of the receptor-linked protein tyrosine phosphatase LAR: proteolytic cleavage and shedding of the CAM-like extracellular region. EMBO J. 11:897-907; Anders L, Mertins P, Lammich S, Murgia M, Hartmann D, Saftig P, Haass C, Ullrich A (2006) Furin-, ADAM 10-, and gamma-secretase-mediated cleavage of a receptor tyrosine phosphatase and regulation of beta-catenin's transcriptional activity. Mol Cell Biol 26:3917-3934; Haapasalo A, Kim D Y, Carey B W, Turunen M K, Pettingell W H, Kovacs D M (2007) Presenilin/gamma-secretase-mediated cleavage regulates association of leukocyte-common antigen-related (LAR) receptor tyrosine phosphatase with beta-catenin. J Biol Chem 282:9063-9072; Chow J P, Fujikawa A, Shimizu H, Noda M (2008) Plasmin-mediated processing of protein tyrosine phosphatase receptor type Z in the mouse brain. Neurosci Lett 442:208-212). These proteins represent additional targets for that can be readily used by the skilled artisan for forming molecular probes that can be used to detect cancers (Barr A J, Ugochukwu E, Lee W H, King O N, Filippakopoulos P, Alfano I, Savitsky P, Burgess-Brown N A, Muller S, Knapp S (2009) Large-scale structural analysis of the classical human protein tyrosine phosphatome. Cell 136:352-363). Furthermore, the targeting peptides can be used as a starting point to develop higher affinity small molecules, antibodies, and/or antibody fragments with similar ligand binding capabilities. The development and screening of small molecules from pharmacophores of the targeting peptides using, for example, in silico screening, can be readily performed, and the binding affinity of such identified molecules can be readily screened against targeting peptides using assays described herein to select small molecule targeting agents.

In certain aspects of the invention, the targeting agent is directly or indirectly labeled with a detectable moiety. The role of a detectable moiety is to facilitate the detection step of a diagnostic method by allowing visualization of the complex formed by binding of the molecular probe to the proteolytically cleaved extracellular fragment of the Ig superfamily cell adhesion molecule. The detectable moiety can be selected such that it generates a signal, which can be measured and whose intensity is related (preferably proportional) to the amount of the molecular probe bound to the tissue being analyzed. Methods for labeling biological molecules, such as polypeptides and antibodies are well-known in the art.

Any of a wide variety of detectable moieties can be used in the practice of the present invention. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some aspects of the invention, the molecular probes described herein may be used in conjunction with non-invasive imaging (e.g., neuroimaging) techniques for in vivo imaging of the molecular probe, such as magnetic resonance spectroscopy (MRS) or imaging (MRI), or gamma imaging, such as positron emission tomography (PET) or single-photon emission computed tomography (SPECT). The term "in vivo imaging" refers to any method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given detectable moiety. For instance, the type of instrument used will guide the selection of the stable isotope. The half-life should be long enough so that it is still detectable at the time of maximum uptake by the target, but short enough so that the host does not sustain deleterious effects.

In one example, the detectable moiety can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the detectable moiety can an include MRS/MRI radiolabel, such as gadolinium, 19F, 13C, that is coupled (e.g., attached or complexed) with the targeting agent using general organic chemistry techniques. The detectable moiety can also include radiolabels, such as 18F, 11C, 75Br, or 76Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The detectable moiety can also include 123I for SPECT. The 123I can be coupled to the targeting agent can by any of several techniques known to the art. See, e.g., Kulkarni, Int. J. Rad. Appl. & Inst. (Part B) 18: 647 (1991), the contents of which are hereby incorporated by reference. In addition, detectable moiety can include any radioactive iodine isotope, such as, but not limited to 131I, 125I, or 123I. The radioactive iodine isotopes can be coupled to the targeting agent by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art.

The detectable moiety can further include known metal radiolabels, such as Technetium-99m (99 mTc). Modification of the targeting agent to introduce ligands that bind such metal ions can be effected without undue experimentation by one of ordinary skill in the radiolabeling art. The metal radiolabeled molecular probes can then be used to detect cancers, such as GBM in the subject. Preparing radiolabeled derivatives of Tc99m is well known in the art. See, for example, Zhuang et al., "Neutral and stereospecific Tc-99m complexes: [99 mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

The molecular probe can be administered to the subject by, for example, systemic, topical, and/or parenteral methods of administration. These methods include, e.g., injection, infusion, deposition, implantation, or topical administration, or any other method of administration where access to the tissue by the molecular probe is desired. In one example, administration of the molecular probe can be by intravenous injection of the molecular probe in the subject. Single or multiple administrations of the probe can be given. "Administered", as used herein, means provision or delivery of a molecular probe in an amount(s) and for a period of time(s) effective to label cancer cells in the subject.

Molecular probes of the present invention can be administered to a subject in a detectable quantity of a pharmaceutical composition containing a molecular probe or a pharmaceutically acceptable water-soluble salt thereof, to a patient. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the molecular probe to the cancer cells.

The molecular probes administered to a subject can be used to determine the presence, location, and/or distribution of cancer cells, i.e., cancer cells associated with proteolytically cleaved extracellular fragments of Ig superfamily cell adhesion molecules, in an organ or body area, such as the brain, of a patient. The presence, location, and/or distribution of the molecular probe in the animal's tissue, e.g., brain tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., brain tissue. The distribution of the molecular probe may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect of the invention, the molecular probes of the present invention may be administered to a subject to assess the distribution GBM cells in a subject's brain and correlate the distribution to a specific location. Neurosurgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of brain on the tumor margin that are outside the tumor edge that appear to be grossly normal but are infiltrated by dispersing tumor cells upon histological examination.

Molecular probes in accordance with the present invention that specifically bind to and/or complex with proteolytically cleaved Ig superfamily cell adhesion molecules (PTPµ) associated with GBM cells can be used in intra-operative imaging techniques to guide neurosurgical resection and eliminate the "educated guess" of the location of the tumor margin by the neurosurgeon. Previous studies have determined that more extensive surgical resection improves patient survival Stummer W, Novotny A, Stepp H, Goetz C, Bise K, Reulen H J (2000) Fluorescence-guided resection of glioblastoma multiforme by using 5-aminolevulinic acid-induced porphyrins: a prospective study in 52 consecutive patients. J Neurosurg 93:1003-1013. Fluorescence-guided resection of glioblastoma multiforme by using 5-aminolevulinic acid-induced porphyrins: a prospective study in 52 consecutive patients. Stummer W, Novotny A, Stepp H, Goetz C, Bise K, Reulen H J (2000) Fluorescence-guided resection of glioblastoma multiforme by using 5-aminolevulinic acid-induced porphyrins: a prospective study in 52 consecutive patients. J Neurosurg 93:1003-1013. Thus, molecular probes that function as diagnostic molecular imaging agents have the potential to increase patient survival rates.

In accordance with another aspect of the invention, the methods and molecular probes described herein can be used to monitor and/or compare the migration, dispersal, and metastases of a cancer in a subject prior to administration of a cancer therapeutic, during administration of a cancer therapeutic, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect of the present invention, a method of monitoring the efficacy of a cancer therapeutic is provided. More specifically the present invention provides for a method of monitoring the efficacy of a cancer therapy.

The method of monitoring the efficacy of a cancer therapeutic can include the steps of administering in vivo to the animal a molecular probe as described herein, then visualizing a distribution of the molecular probe in the animal (e.g., with an in vivo imaging modality as described herein), and then correlating the distribution of the molecular probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a molecular probe pre and post cancer therapy.

In certain embodiments of the invention, the methods and molecular probes of the present invention can be used to measure the efficacy of therapeutic administered to a subject for treating glioblastoma multiforme. In this embodiment, the molecular probe can be administered to the subject prior to, during, or post administration of the therapeutic regimen and the distribution of glioblastoma multiforme cells can be imaged to determine the efficacy of the therapeutic regimen. In one example, the therapeutic regimen can include a surgical resection of the glioblastoma multiforme and the molecular probe can be used to define the distribution of the glioblstoma multiforme pre-operative and post-operative to determine the efficacy of the surgical resection. Optionally, the methods and molecular probes of the present invention can be used in an intra-operative surgical procedure, such as a surgical tumor resection, to more readily define and/or image the cancer cell mass or volume during the surgery.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example

We recently found that normal brain and primary rat astrocytes express PTPµ, but the most dispersive glial tumors, GBMs, downregulate PTPµ expression. The downregulation of PTPµ occurs via proteolytic cleavage in human GBM tumors, which may be an important event that dysregulates normal contact inhibition of movement. In this example, it is demonstrated that PTPµ proteolytic cleavage generates an extracellular fragment of PTPµ in human GBM tumors that is retained in the tumor microenvironment. This extracellular fragment contains the domains required for efficient PTPµ-mediated homophilic cell-cell adhesion. We devised a strategy to detect this PTPµ extracellular fragment by generating a series of fluorescently tagged peptide probes to surface-exposed sites of PTPµ, based on crystallographic data (Aricescu A R, Hon W C, Siebold C, Lu W, van der Merwe P A, Jones E Y (2006) Molecular analysis of receptor protein tyrosine phosphatase mu-mediated cell adhesion. Embo J 25:701-712.; Aricescu A R, Siebold C, Choudhuri K, Chang V T, Lu W, Davis S J, van der Merwe P A, Jones E Y (2007) Structure of a tyrosine phosphatase adhesive interaction reveals a spacer-clamp mechanism. Science 317: 1217-1220.; Aricescu A R, Siebold C, Jones E Y (2008)

Receptor protein tyrosine phosphatase micro: measuring where to stick. Biochem Soc Trans 36:167-172). The peptide probes specifically recognized primary human GBM cells in tissue sections of surgically resected tumor. More importantly, the peptides recognized GBM tumors in vivo in two different human GBM xenografts in nude mice, and are capable of crossing the blood-brain bather to label intracranial GBM tumors. These results indicate that the cleaved PTPμ extracellular fragment remains associated with the GBM microenvironment and is a unique biomarker of GBM cells that can be used as a molecular diagnostic imaging agent to detect the tumor margin of human glioblastomas in vivo.

Materials and Methods

Peptide Synthesis and Conjugation

SBK1 (SEQ ID NO: 4), SBK2 (SEQ ID NO: 5), SBK3 (SEQ ID NO: 6) and SBK4 (SEQ ID NO: 7) peptides were synthesized either on an Applied Biosystems model 433A synthesizer or were purchased from Genscript Corporation (Piscataway, N.J., USA). Following synthesis, the N-terminal glycine residue of each peptide was specifically coupled to Texas Red-X (mixed isomers) or Alexa-750 succinimidyl ester dye (Molecular Probes Inc., Eugene, Oreg.), which has a five-carbon spacer between the succinimide group that couples to the N-terminal amine and the fluorophore.

Human Brain Tissue Protein Extraction

Using a FDA-approved computer navigational device and software (BrainLab Vector Vision 2 and i-Plan 2.0) the neurosurgeon co-registered multiple scalp points with volumetric RAGE T1±Gadolinium MRI (1.5 mm segments/0 skips) obtained the day prior to surgery using a standard technique (Z-Touch). After achieving precision of <1 mm and confirmation using various objective skull landmarks, surgery was performed using stereotactic techniques. After pathological confirmation of GBM was obtained, the stereotactic device was used to identify the edge and center of the Gadolinium enhanced tumor mass and paired specimens of approximately 100 mg each were preserved in liquid nitrogen or formalin-paraffin, respectively. In some cases, non-eloquent brain was also identified and similarly preserved if it was part of the region to be resected. Similarly, discarded tissue from patients undergoing cortical resections for intractable epilepsy was collected for noncancerous "normal" tissue after the neuropathologists released the sample. Following tissue resection, the samples were snap frozen, thawed on ice in lysis buffer and protein was extracted as previously described. Mouse flank Gli36Δ5 or LN-229 tumors were excised, snap frozen, then lysed using a PRO 200 tissue tearor (PRO Scientific Inc., Monroe, Conn., USA). All samples were separated by SDS-PAGE and transferred to nitrocellulose for immunoblotting with antibodies against the extracellular segment of PTPμ (BK9) (Brady-Kalnay S M, Tonks N K (1994) Identification of the homophilic binding site of the receptor protein tyrosine phosphatase PTPμ. J Biol Chem 269:28472-28477).

Peptide Labeling of Human Brain Tissue

Human glioblastoma or noncancerous "normal" epilepsy tissue samples were immediately fixed in 10% neutral buffered formalin (Sigma-Aldrich, USA). Tissues were ethanol dehydrated and paraffin embedded. Tissue sections were cut at 5 μm intervals and stored at room temperature (RT). Before staining, tissue sections were deparaffinized and blocked with 2% goat serum in PBS for 20 minutes at RT. PTPμ-TR peptides were diluted in block buffer and incubated with the tissue sections for 1 hour at RT in the dark. The sections were rinsed with PBS, coverslipped with Citifluor Antifadent Mounting Medium, AF1 (Electron Microscopy Sciences, Hatfield, Pa.) and imaged immediately at 40× on a Nikon TE-200 inverted microscope, using a SPOT-RT camera and SPOT software version 3.2 (Diagnostic Instruments, Inc., Sterling Heights, Mich.). High magnification phase and fluorescent images were taken using the same exposure settings between multiple experiments. The working concentrations for the peptides were determined empirically for tissue staining and are as follows: SBK1-TR, 40 μM; SBK2-TR, 10 μM; SBK3-TR, 10 μM; and SBK4-TR, 3.3 μM. The SBK4-TR peptide was the most effective in labeling tissue sections.

Antibody Blocking Experiments

To block PTPμ binding sites, human tumor tissue sections were pre-incubated for 1 hour at RT with BK2 monoclonal antibody, raised against the MAM domain of PTPμ (Brady-Kalnay S M, Tonks N K (1994) Identification of the homophilic binding site of the receptor protein tyrosine phosphatase PTPμ. J Biol Chem 269:28472-28477), prior to incubation with SBK2-TR (10 μM) or SBK4-TR (3.3 μM) peptide in block buffer for 1 hour at RT in the dark. Tissue sections were rinsed and imaged as described above.

Heterotopic Xenograft Tumors

Human Gli36Δ5 glioblastoma cells constitutively overexpress the vIII mutant forms of the EGFR gene (Tyminski E, Leroy S, Terada K, Finkelstein D M, Hyatt J L, Danks M K, Potter P M, Saeki Y, Chiocca E A (2005) Brain tumor oncolysis with replication-conditional herpes simplex virus type 1 expressing the prodrug-activating genes, CYP2B 1 and secreted human intestinal carboxylesterase, in combination with cyclophosphamide and irinotecan. Cancer Res 65:6850-6857). Human LN-229 glioblastoma cells were obtained from American Type Culture Collection, Manassas, Va. Gli36Δ5 or LN-229 cells were harvested for flank implantation by trypsinization. In some experiments, the cells were infected with lentivirus to express GFP (Tyagi M, Karn J (2007) CBF-1 promotes transcriptional silencing during the establishment of HIV-1 latency. EMBO J. 26:4985-4995) 48 hours prior to harvesting. The cells (2×106 cells for flank tumor implants) were re-suspended in a 1:1 dilution of PBS and Matrigel (BD Biosciences; Franklin Lakes, N.J.) for a total volume of 250-300 μL per flank tumor implant per animal.

NIH athymic nude female mice (5-8 weeks and 20-25 g upon arrival, NCl—NIH) were obtained. All animal protocols were IACUC approved. For flank tumor implants, mice were anesthetized with inhaled isofluorane:oxygen for immobilization. The Matrigel: cell mixture was loaded into a 1 mL syringe fitted with a 26-gauge needle and kept on ice. The mixture was injected subcutaneously in the right flank region of the mouse.

Peptide Labeling of Mouse Flank Tumor Sections

NIH athymic nude female mice implanted with Gli36Δ5 or LN-229 flank tumors for 2 to 3 weeks were anesthetized with inhaled isoflurane: oxygen and sacrificed by decapitation. Flank tumors were then excised, fixed in 4% paraformaldehyde in PEM buffer (80 mM Pipes, 5 mM EGTA, 1 mM Magnesium Chloride, 3% sucrose), pH 7.4, embedded in OCT and cryosectioned at 5 μm intervals. Slides were stored at −20° C. For peptide labeling experiments, the slides were thawed and incubated with peptide diluted to 100-200 μM as described above.

In Vivo Imaging of Flank Tumors

Nude mice with Gli36Δ5 or LN-229 flank tumors were imaged at 9-28 days after cell injection. Fluorophore-conjugated PTPμ peptides were diluted to 100 μM (SBK2-Alexa) or 200 μM (SBK1-TR, SBK3-TR, SBK4-TR, Scrambled SBK2-TR control peptide) in PBS and injected (total volume of 150 µL) via a lateral tail vein using a 28-gauge insulin syringe. In the animals containing GFP-expressing tumor cells, Alexa-750 labeled peptide was used due to its limited spectral overlap with GFP. Spectral fluorescence images were obtained using the Maestro™ FLEX In-Vivo Imaging System using the appropriate filters for GFP (tumor; Ex445-490 nm, Em 515 longpass filter; acquisition settings 500-720 in 10 nm steps), Texas Red (peptide; Ex 575-605 nm, Em 645; acquisition settings 630-850 in 10 nm steps) or Alexa-750 (peptide; Ex 671-705 nm, Em 750 longpass filter; acquisition settings 730-950 in 10 nm steps). Acquisition settings were 53 milliseconds for GFP and 1000 milliseconds for either Texas Red or Alexa-750 labeled peptide. Prior to peptide injection, background images were acquired through the skin to provide autofluorescence spectra. Following peptide injection, fluorescence images were acquired at 5 to 15 minute intervals over the course of 2 to 3 hours. The multispectral fluorescence images were background subtracted and unmixed, using Maestro™ software (Cambridge Research & Instrumentation, Inc. (CRi), Woburn, Mass.), to spectrally separate the autofluorescence animal signal from the peptide signals. Regions of interest (ROI) were selected over the tumor or non-tumor skin. Pixel values for the peptide signal, in photons measured at the surface of the animal, were determined within these ROI. Higher pixel values corresponded to presence of tumor. Pixel values in the tumor ROI were normalized to the non-tumor ROI and peptide concentration, and then plotted. Each PTPµ peptide was tested on a minimum of three animals containing Gli36Δ5 and three animals containing LN-229 flank tumors. Statistical analyses were performed using Microsoft Excel and an unpaired student t test.

Orthotopic Xenograft Tumors

Gli36Δ5-GFP cells were harvested for intracranial implantation by trypsinization and concentrated to $1 \times 10^5$ cells per µL of PBS. For brain tumor implants, NIH athymic nude female mice were anesthetized by intraperitoneal injection of 50 mg/kg ketamine/xylazine and fitted into a stereotaxic rodent frame (David Kopf Instruments, Tujunga, Calif.). A small incision was made just lateral to midline to expose the bregma suture. A small (0.7 mm) burr hole was drilled at AP=+1, ML=−2.5 from bregma. Glioblastoma cells were slowly deposited at a rate of 1 µl/minute in the right striatum at a depth of −3 mm from dura with a 10 µL syringe (26G needle; Hamilton Company; Reno, Nev.). The needle was slowly withdrawn and the incision was closed with sutures.

In Vivo Imaging of Intracranial Tumors

Nude mice with Gli36Δ5-GFP intracranial tumors were imaged at 9-12 days after GBM cell implant. Fluorophore-conjugated PTPµ peptides were injected via tail vein as described above. Following a 25 minute incubation for clearance of unbound PTPµ peptide, the animals were sacrificed, the brains were removed and coronal sections made at 1 mm intervals. Individual brain sections containing tumor were placed on a black slide and examined using the Maestro™ FLEX In-Vivo Imaging System as described above. Untreated brains containing Gli36Δ5-GFP intracranial tumors were used to provide autofluorescence spectra. ROI were selected over the tumor region in each brain slice. Pixel values for the peptide signal, in photons measured from the slice, were determined within these ROI. The multispectral fluorescence images were background subtracted and analyzed using the Maestro™ software as described above. Statistical analyses were performed using Microsoft Excel and an unpaired student t test.

Results

An extracellular fragment of PTPµ is detected in human glioblastomas. We show a 55 kDa N-terminal extracellular fragment of PTPµ is retained in the GBM samples, as shown by immunoblotting with an antibody against the extracellular segment of PTPµ (FIG. 1A). Based on size, and antibody recognition using antibodies against the MAM domain of PTPµ, this fragment likely contains the MAM, Ig and the first two FNIII repeats (FIG. 2A). The 55 kDa extracellular fragment of PTPµ is retained in the center and edge of the resected GBM tumor but not substantially in normal cortical brain tissue from the same patient (FIG. 1A). The human edge samples contain very few tumor cells proportionally to normal cells, suggesting that the PTPµ extracellular fragment is concentrated at the tumor edge and may be exploitable as a biomarker of the tumor margin.

Peptide Design and Optimization

The homophilic binding of PTPµ has been shown to require the domains that are present in the 55 kDa cleaved fragment (Brady-Kalnay S M, Tonks N K (1994) Identification of the homophilic binding site of the receptor protein tyrosine phosphatase PTPµ. J Biol Chem 269:28472-28477); Zondag G, Koningstein G, Jiang Y P, Sap J, Moolenaar W H, Gebbink M (1995) Homophilic interactions mediated by receptor tyrosine phosphatases µ and κ. J Biol Chem 270: 14247-14250; Cismasiu V B, Denes S A, Reilander H, Michel H, Szedlacsek S E (2004) The MAM (meprin/A5-protein/PTPmu) domain is a homophilic binding site promoting the lateral dimerization of receptor-like protein-tyrosine phosphatase mu. J Biol Chem 279:26922-26931.; Del Vecchio R L, Tonks N K (2005) The conserved immunoglobulin domain controls the subcellular localization of the homophilic adhesion receptor protein-tyrosine phosphatase mu. J Biol Chem 280:1603-1612; Aricescu A R, Hon W C, Siebold C, Lu W, van der Merwe P A, Jones E Y (2006) Molecular analysis of receptor protein tyrosine phosphatase mu-mediated cell adhesion. Embo J 25:701-712; Aricescu A R, Siebold C, Choudhuri K, Chang V T, Lu W, Davis S J, van der Merwe P A, Jones E Y (2007) Structure of a tyrosine phosphatase adhesive interaction reveals a spacer-clamp mechanism. Science 317:1217-1220; Aricescu A R, Siebold C, Jones E Y (2008) Receptor protein tyrosine phosphatase micro: measuring where to stick. Biochem Soc Trans 36:167-172. Based upon crystallographic data indicating which residues are surface exposed (Aricescu A R, Hon W C, Siebold C, Lu W, van der Merwe P A, Jones E Y (2006) Molecular analysis of receptor protein tyrosine phosphatase mu-mediated cell adhesion. Embo J 25:701-712.; Aricescu A R, Siebold C, Choudhuri K, Chang V T, Lu W, Davis S J, van der Merwe P A, Jones E Y (2007) Structure of a tyrosine phosphatase adhesive interaction reveals a spacer-clamp mechanism. Science 317:1217-1220), and our binding studies (Brady-Kalnay S M, Tonks N K (1994) Identification of the homophilic binding site of the receptor protein tyrosine phosphatase PTPµ. J Biol Chem 269:28472-28477), we designed peptide probes to bind homophilically and recognize the adhesive domains contained within the cleaved fragment of the extracellular segment of PTPµ (FIGS. 2A, B). Four peptides derived from the MAM (SBK1 (SEQ ID NO: 4) and SBK2 (SEQ ID NO: 5) peptides) or Ig (SBK3 (SEQ ID NO: 6) and SBK4 (SEQ ID NO: 7) domains of PTPµ were generated (FIGS. 2A, B). As a control, a scrambled version of the SBK2 peptide was also synthesized. The peptides were fluorescently labeled with Texas Red-X succinimidyl ester dye on the N-terminus. Effective peptide concentrations for tissue labeling were determined by dilution histochemical analyses using human GBM tissue sections and indicated that a range of 3-40 µM was effective.

Detection of Human Glioblastomas with the PTPμ Peptide Probes

Figure 4:
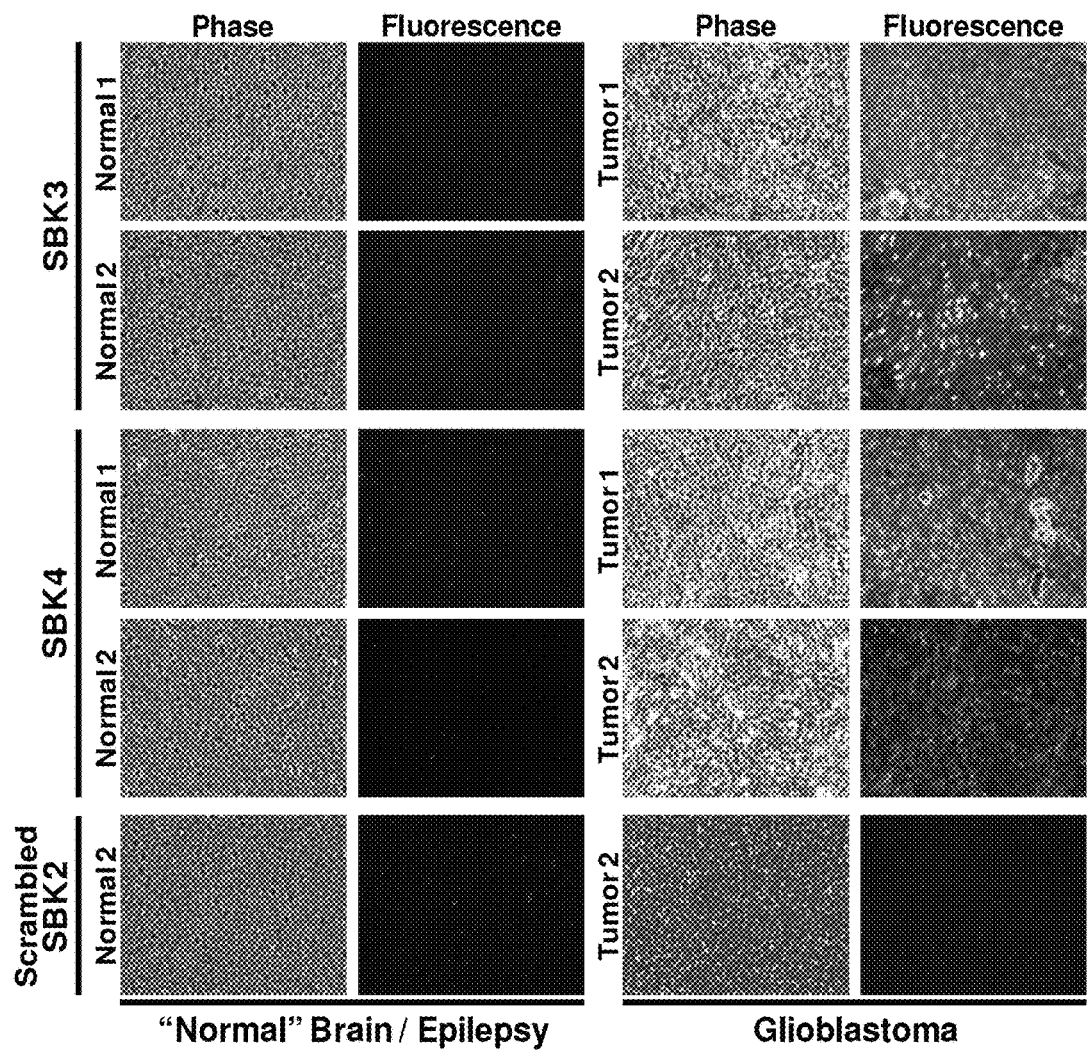
FIG. 4 illustrates images showing SBK3 (SEQ ID NO: 6) and SBK4 (SEQ ID NO: 7) peptide probes specifically recognize human glioblastoma tissue but not normal brain. Sections of noncancerous normal cortical brain tissue from epilepsy patients or GBM tumor were histochemically labeled with Texas Red-conjugated SBK3 (SEQ ID NO: 6), SBK4 (SEQ ID NO: 7) or Scrambled SBK2 peptide. Two examples of normal and GBM tissue are shown that are representative of 6 different samples examined.

To examine the localization of the 55 kDa PTPμ fragment within GBM tumors, the Texas Red (TR) conjugated peptides were used as probes to label sections of GBM or noncancerous human brain obtained from epilepsy patients. The PTPμ-TR peptides, SBK2, SBK3 and SBK4 each recognized GBM tissue to varying degrees, although the best labeling occurred with peptides SBK2 and SBK4 (FIGS. 3, 4). The SBK1 peptide did not substantially label either the noncancerous human brain or GBM (FIG. 3). The SBK2, SBK3 and SBK4 peptides typically labeled the parenchyma above background with particularly bright labeling of the cell bodies. Endothelial cells lining blood vessels were also brightly labeled within the tumor (FIG. 4). Endothelial cells express high levels of PTPμ (Campman M, Yoshizumi M, Seidah N G, Lee M E, Bianchi C, Haber E (1996) Increased proteolytic processing of protein tyrosine phosphatase μ in confluent vascular endothelial cells: the role of PC5, a member of the subtilisin family. Biochemistry 35:3797-3802; Bianchi C, Sellke F W, Neel B G (1999) Receptor-Type Protein-Tyrosine Phosphatase mu Is Expressed in Specific Vascular Endothelial Beds in vivo. Experimental cell research 248:329; Koop E A, Lopes S M, Feiken E, Bluyssen H A, van der Valk M, Voest E E, Mummery C L, Moolenaar W H, Gebbink M F (2003) Receptor protein tyrosine phosphatase mu expression as a marker for endothelial cell heterogeneity; analysis of RPTPmu gene expression using LacZ knock-in mice. Int J Dev Biol 47:345-354; Koop E A, Gebbink M F, Sweeney T E, Mathy M J, Heijnen H F, Spaan J A, Voest E E, VanBavel E, Peters S L (2005) Impaired flow-induced dilation in mesenteric resistance arteries from receptor protein tyrosine phosphatase-mu-deficient mice. Am J Physiol Heart Circ Physiol 288:H1218-1223; Sui X F, Kiser T D, Hyun S W, Angelini D J, Del Vecchio R L, Young B A, Hasday J D, Romer L H, Passaniti A, Tonks N K, Goldblum S E (2005) Receptor protein tyrosine phosphatase mu regulates the paracellular pathway in human lung microvascular endothelia. Am J Pathol 166:1247-1258). PTPμ present on the surface of endothelial cells may also be proteolyzed in the tumor microenvironment. Two representative GBM tumors are shown (Tumor 1 and Tumor 2). Similar results were observed in six different GBM samples (data not shown). In contrast, scrambled control peptide (Scrambled SBK2) did not label the GBM tissue (FIGS. 3, 4). When PTPμ peptides were incubated with sections of noncancerous brain tissue obtained from epilepsy patients, no specific structures were labeled in either white or gray matter regions (FIGS. 3, 4). Similar results were observed in six different samples of noncancerous "normal brain" (data not shown). PTPμ protein is highly expressed in normal brain and plays a role in stabilization of cell-cell contacts (Burden-Gulley S M, Brady-Kalnay S M (1999) PTPμ regulates N-cadherin-dependent neurite outgrowth. J Cell Biol 144:1323-1336; Burgoyne A M, Palomo J M, Phillips-Mason P J, Burden-Gulley S M, Major D L, Zaremba A, Robinson S, Sloan A E, Vogelbaum M A, Miller R H, Brady-Kalnay S M (2009b) PTPmu suppresses glioblastoma cell migration and dispersal. Neuro-Oncology, March 20 Epub ahead of print). When PTPμ is involved in cell-cell adhesion, its binding sites may be fully engaged and therefore unavailable for recognition by the PTPμ peptides. Alternatively, in GBM tissue, the cleaved 55 kDa extracellular domain of PTPμ may undergo a conformational change that allows recognition by the PTPμ peptides. Together, these results show that these PTPμ peptides can be used for detection of human glioblastoma tissue.

Figure 5:
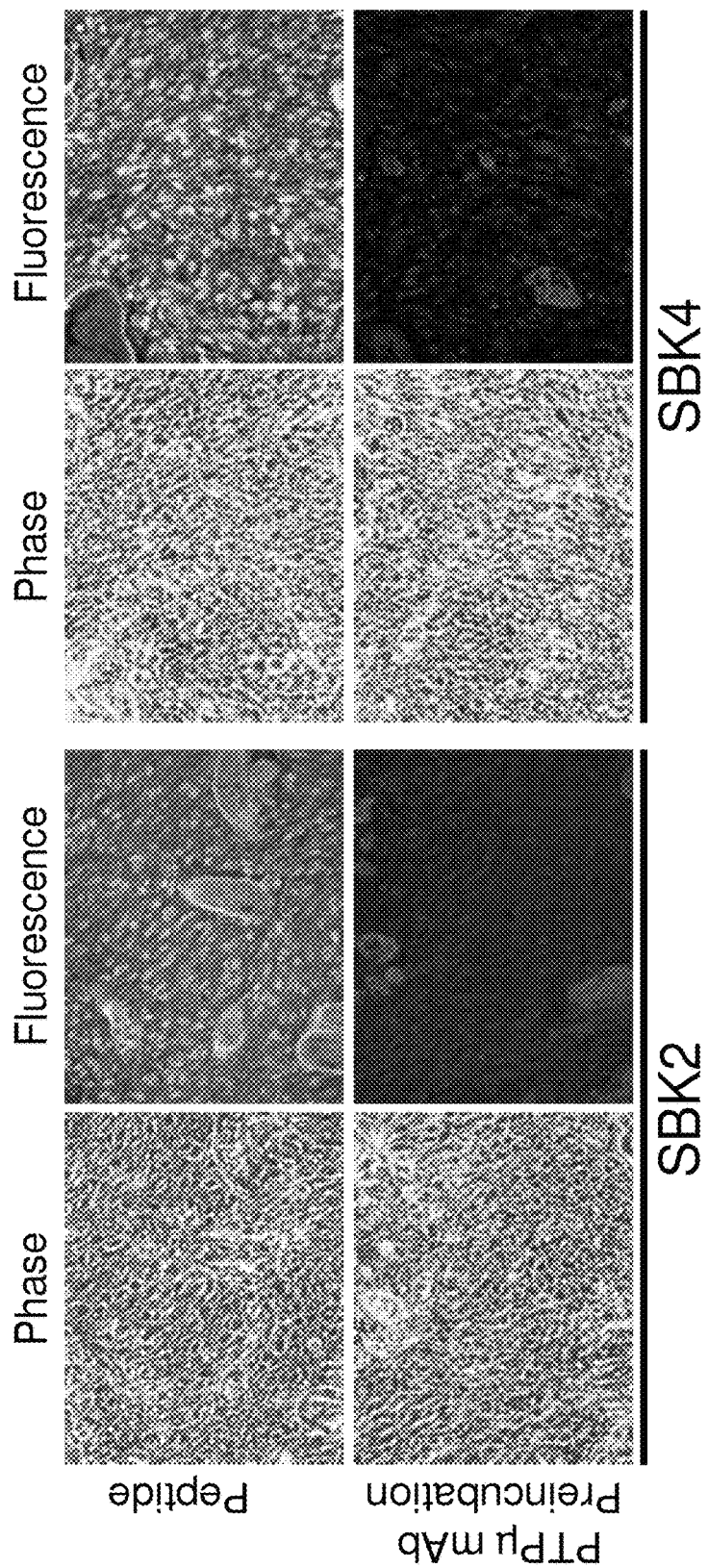
FIG. 5 illustrates images showing PTPµ mAb blocks SBK2 (SEQ ID NO: 5) and SBK4 (SEQ ID NO: 7) peptide binding to human glioblastoma tissue. Preincubation of a PTPµ extracellular antibody raised against the MAM domain (BK2) specifically blocked SBK2-TR (SEQ ID NO: 5) and SBK4-TR (SEQ ID NO: 7) peptide binding to GBM tumor tissue sections.

The PTPμ peptides specifically recognize PTPμ. To confirm that the PTPμ peptides were binding to the 55 kDa PTPμ extracellular fragment in GBM, we performed antibody-blocking experiments. GBM tissue sections were pre-incubated with BK2 monoclonal antibody raised against the MAM domain of PTPμ (Brady-Kalnay S M, Tonks N K (1994) Identification of the homophilic binding site of the receptor protein tyrosine phosphatase PTPμ. J Biol Chem 269:28472-28477) prior to incubation with the SBK2 or SBK4 peptides, which were generated from either the MAM or Ig domains of PTPμ, respectively. Preincubation with BK2 monoclonal antibody caused a complete block of SBK2 and SBK4 peptide binding (FIG. 5). Although SBK4 is derived from the Ig domain of PTPμ, steric hindrance by the large BK2 antibody likely prevented the SBK4 peptide from reaching its binding site on the Ig domain, which is in close proximity to the MAM domain, the target of BK2 (J Biol Chem 269:28472-28477). The PTPμ antibody-mediated block of peptide binding suggests that the peptides are recognizing the extracellular fragment of PTPμ in human GBM tissues.

Peptide recognition of glioblastoma associated proteins as a diagnostic tool. Specific recognition of GBM cells in vivo through peptide binding would provide a powerful diagnostic tool. We recently observed a dramatic reduction in full length PTPμ protein in the highly migratory LN-229 human GBM cell line due to proteolysis (Burgoyne A M, Palomo J M, Phillips-Mason P J, Burden-Gulley S M, Major D L, Zaremba A, Robinson S, Sloan A E, Vogelbaum M A, Miller R H, Brady-Kalnay S M (2009b) PTPmu suppresses glioblastoma cell migration and dispersal. Neuro-Oncology, March 20 Epub ahead of print; Burgoyne A M, Phillips-Mason P J, Burden-Gulley S M, Robinson S, Sloan A E, Miller R H, Brady-Kalnay S M (2009a) Proteolytic Cleavage of PTPmu Regulates Glioblastoma Cell Migration. Cancer Research In press). For this manuscript, an animal model system of GBM was developed for in vivo labeling. Two human glioblastoma cell lines, LN-229 and Gli36Δ5, were injected individually into the flanks of nude mice for the production of xenograft tumors. At 2-3 weeks post-injection, the tumors were excised and homogenized for biochemical analysis. The 55 kDa fragment of PTPμ is present in both LN-229 and Gli36Δ5 cells when grown as flank tumors (FIG. 1B).

Figure 6:
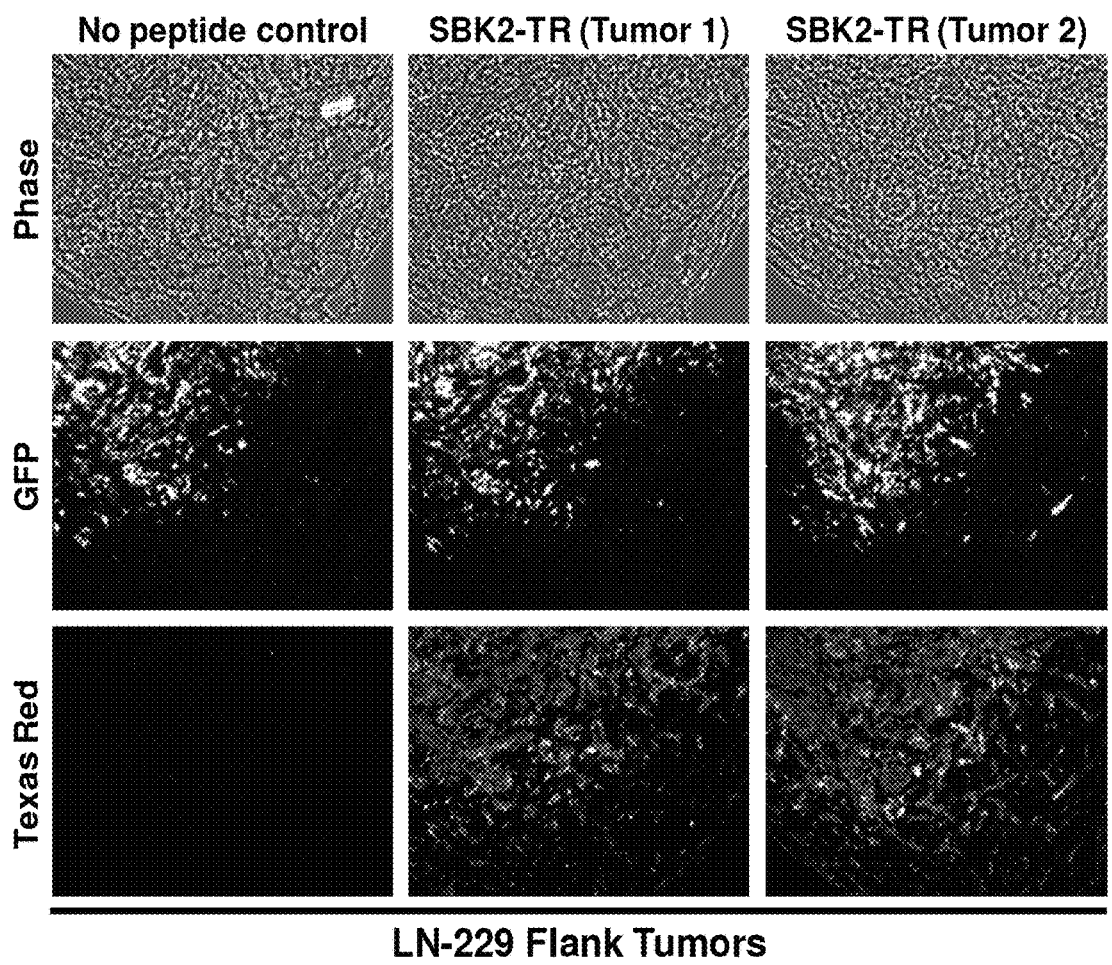
FIG. 6 illustrates images showing small cell clusters from LN-229 flank tumors label with PTPµ peptide SBK2 (SEQ ID NO: 5). Flank tumors of LN-229 cells were excised, fixed and sectioned. The LN-229 cells express GFP. Binding of the Texas Red-conjugated SBK2 peptide is shown in two tumor samples. SBK2 peptide (SEQ ID NO: 5) labels small clusters of cells in the tumor microenvironment.
Figure 10:
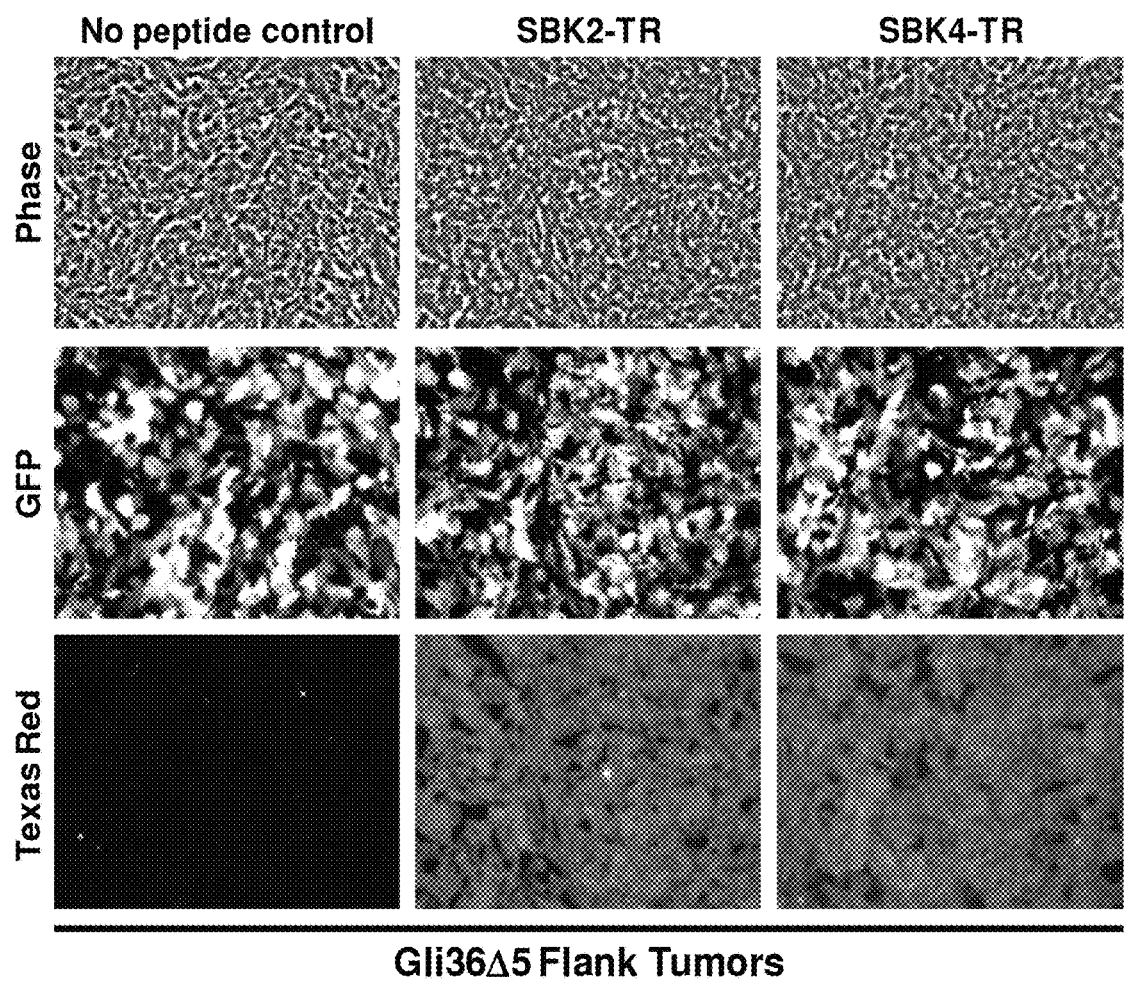
FIG. 10 illustrates images showing Gli36Δ5 flank tumors label with PTPµ peptides. Flank tumors of Gli36Δ5 cells were excised, fixed and sectioned. The Gli36Δ5 cells express GFP. Binding of the Texas Red-conjugated SBK2 (SEQ ID NO: 5) and SBK4 peptides (SEQ ID NO: 7) is shown. The peptides label both the tumor cells and the extracellular spaces in the tumor microenvironment.
Figure 11:
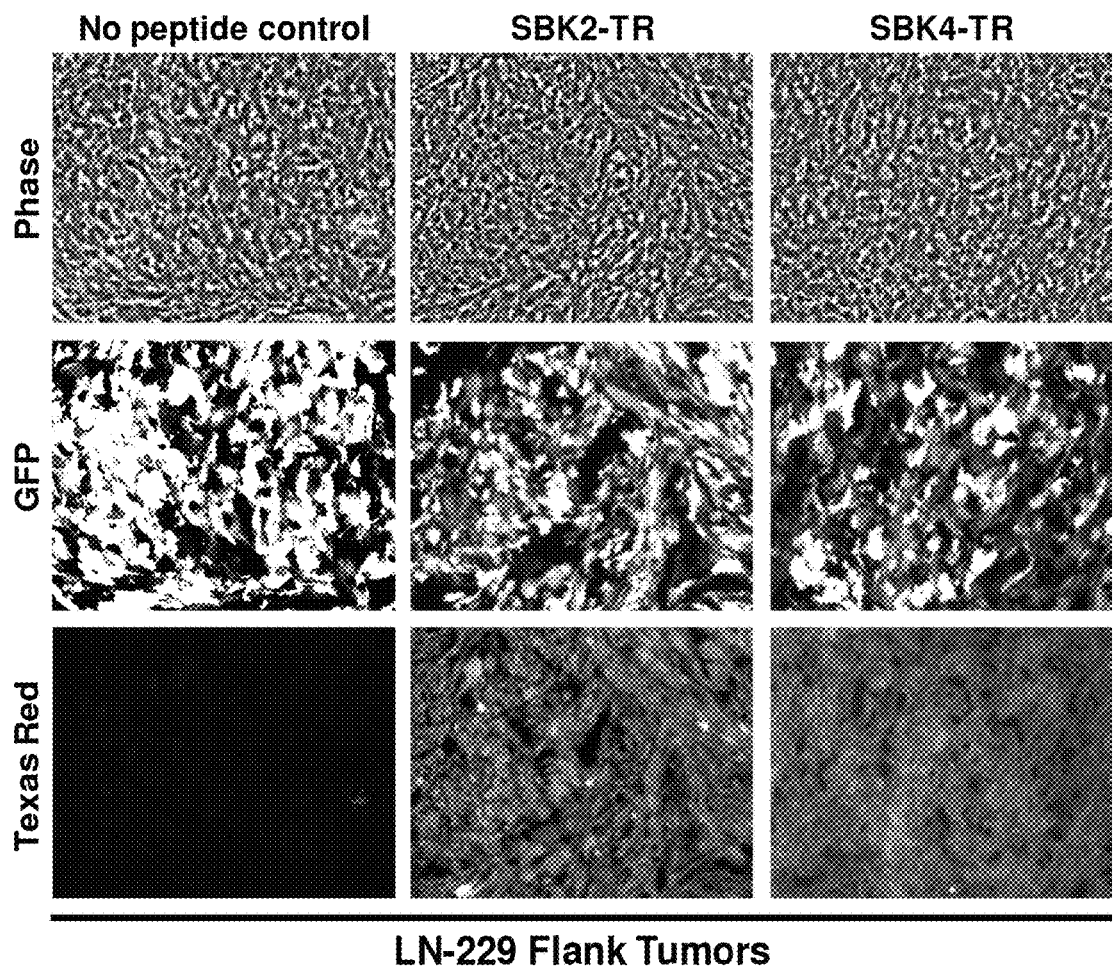
FIG. 11 illustrates images showing LN-229 flank tumors label with PTPµ peptides. Flank tumors of LN-229 cells were excised, fixed and sectioned. The LN-229 cells express GFP. Binding of the Texas Red-conjugated SBK2 (SEQ ID NO: 5) and SBK4 peptides (SEQ ID NO: 7) is shown. The peptides label both the tumor cells and the extracellular spaces in the tumor microenvironment.

To observe localization of the 55 kDa fragment in the xenograft tumors, sections of fixed tumors were incubated with either SBK2 or SBK4 peptides. The PTPμ peptides labeled both the Gli36Δ5 (FIG. 10) and LN-229 (FIG. 11) tumors, in a pattern that closely overlaid the cells of the tumors, as evidenced by GFP fluorescence, but also was observed in some intercellular spaces. This result is not unexpected since the extracellular fragment of PTPμ is likely shed by the tumor cells. Small clusters of labeled cells were clearly visible in the tumor microenvironment (FIG. 6), thus the peptides are useful for detection of dispersing cells. The recognition of the 55 kDa fragment by PTPμ peptides suggested that this animal model was a viable system for further study in vivo.

Figure 7:
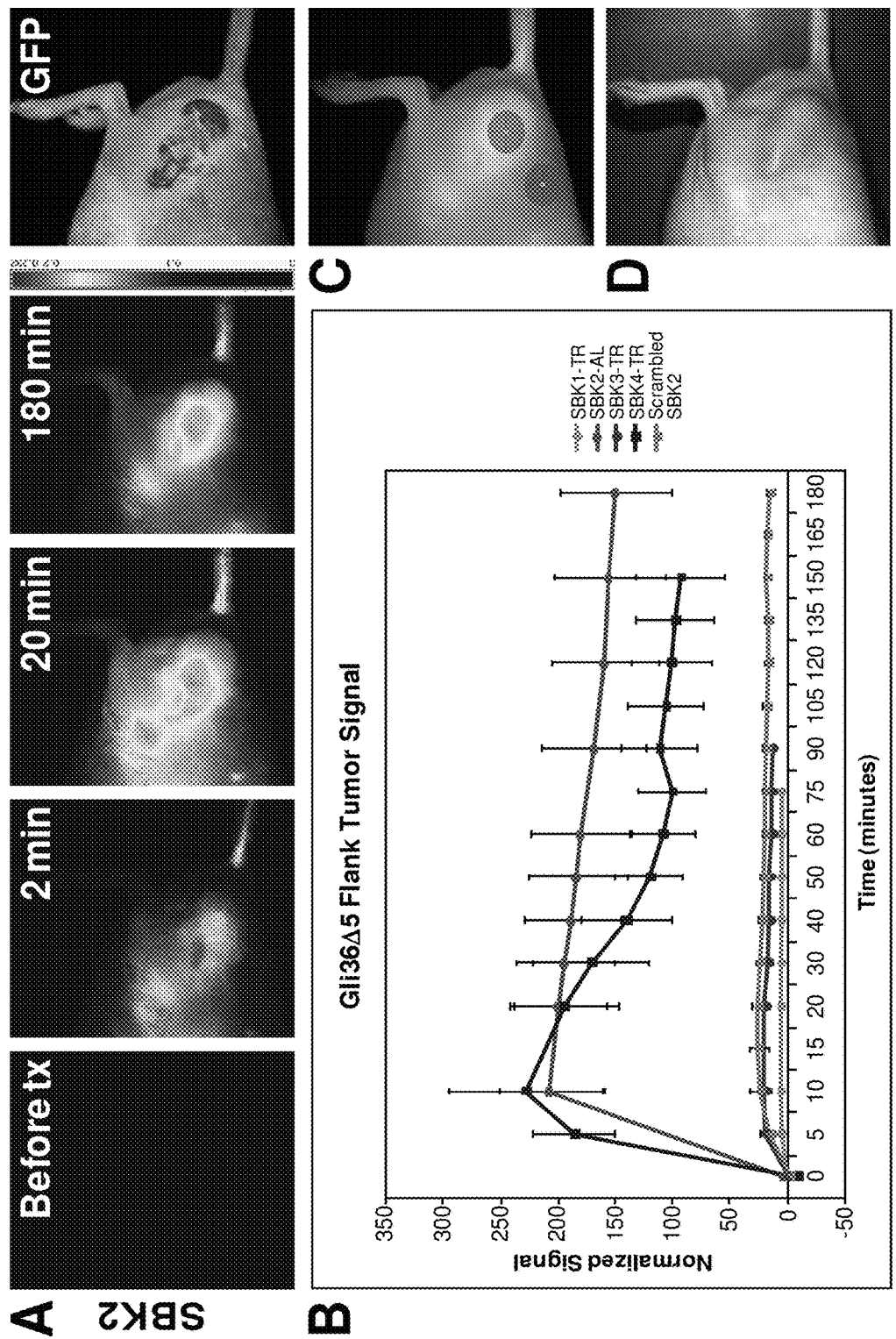
FIG. 7 illustrates images showing PTPµ peptides SBK2 (SEQ ID NO: 5) and SBK4 (SEQ ID NO: 7) recognize Gli36Δ5 mouse flank tumors in vivo. Texas Red (TR) or Alexa (AL)-conjugated PTPµ peptides were administered intravenously to mice with xenograft flank tumors of Gli36Δ5 cells. (A) Fluorescent images of SBK2-AL peptide labeling. Panel labeled "before tx" (before time course) shows the animal autofluorescent background. The tumor cells are expressing GFP. (B) Time course of peptide binding to flank tumors (N=3 animals tested per peptide). Average normalized signals acquired in the tumor region of interest were plotted. The error bars represent standard error of the mean from the 3 animals. (C) Regions of interest shown over the tumor and non-tumor skin. (D) Bright field image of the flank tumor labeled in (A).
Figure 8:
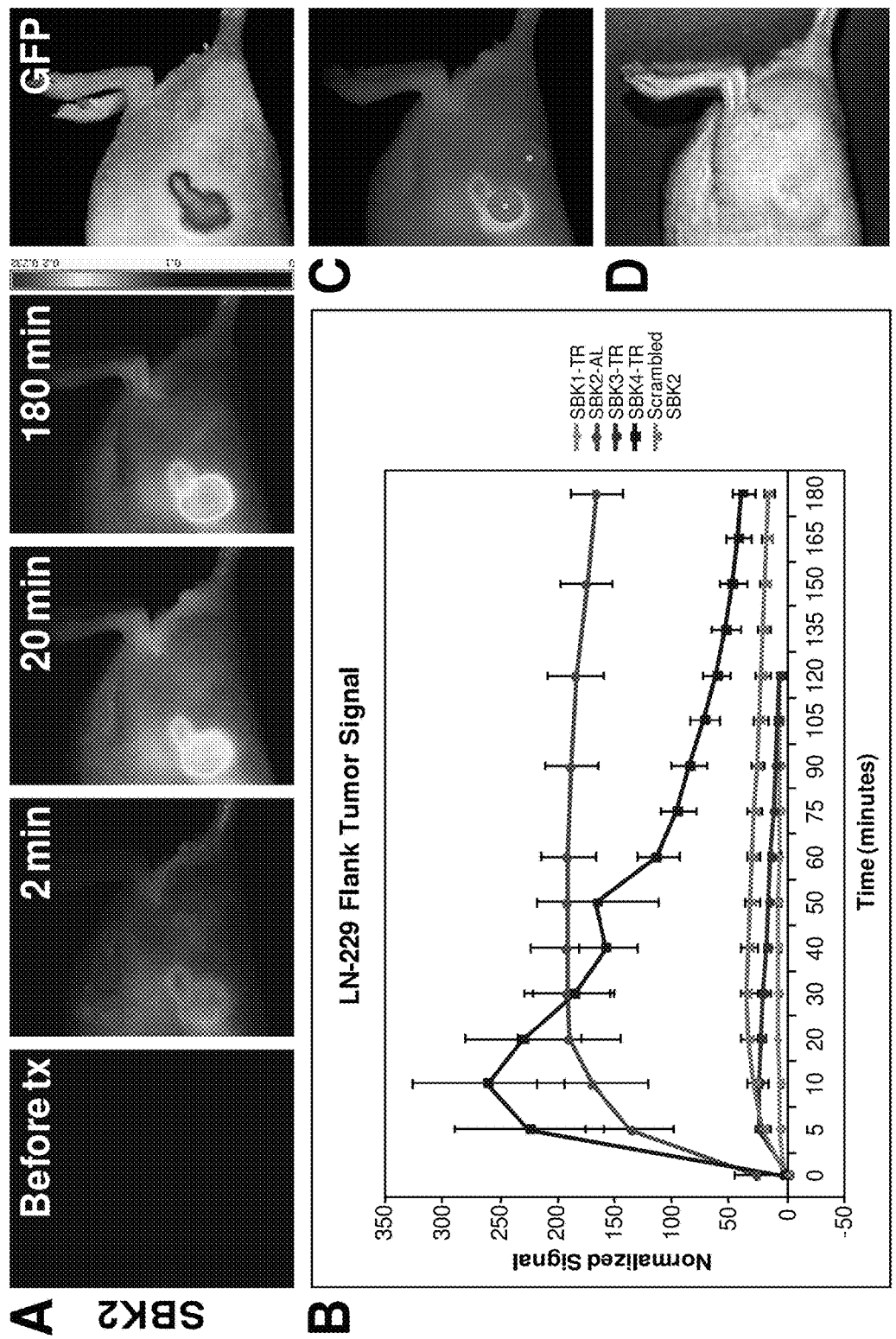
FIG. 8 illustrates images showing PTPµ peptides SBK2 (SEQ ID NO: 5) and SBK4 (SEQ ID NO: 7) recognize LN-229 mouse flank tumors in vivo. Texas Red (TR) or Alexa (AL)-conjugated PTPµ peptides were administered intravenously to mice with xenograft flank tumors of LN-229 cells. (A) Fluorescent images of SBK2-AL peptide labeling. Panel labeled "before tx" (before time course) shows the animal autofluorescent background. The tumor cells are expressing GFP. (B) Time course of peptide binding to flank tumors (N=3 animals tested per peptide). Average normalized signals acquired in the tumor region of interest were plotted. The error bars represent standard error of the mean from the 3 animals. (C) Regions of interest shown over the tumor and non-tumor skin. (D) Bright field image of the flank tumor labeled in (A).

Flank tumors provide a useful model for molecular imaging studies due to accessibility and ease of imaging using fluorescence detection methods. Nude mice with Gli36Δ5 or LN-229 flank xenografts were imaged through the skin with the Maestro™ FLEX In-Vivo Imaging System using the appropriate filters for GFP, Texas Red or Alexa-750. Background images of the flank region containing the tumor were acquired, PTPμ peptides were administered via tail vein injection, and the animals were imaged at regular intervals over the course of 2 to 3 hours. Fluorescence was observed throughout the animals within one minute after injection, but maximal tumor labeling occurred within 10 to 20 minutes after injection. Of interest, the tumor microenvironment was also labeled, showing that the PTPμ fragment remains associated with the cells at the tumor edge. Unbound circulating peptide was cleared from the animals quickly, resulting in a clear demarcation of tumor over the normal tissue background (FIGS. 7A, 8A). In most cases, the tumor remained labeled above background for at least 3 hours. The average signal in the tumor was normalized to the average signal in non-tumor skin and plotted (FIGS. 7B and 8B). SBK2 peptide rapidly bound to the Gli36Δ5-GFP tumor and remained bound at a level greater than in the surrounding skin over the course of the three-hour experiment (FIG. 7). Peak levels of Gli36Δ5-GFP tumor labeling were achieved by 10-20 minutes. Of note, similar results were obtained when the tumor was composed of LN-229-GFP human GBM cell line (FIG. 8), suggesting that the peptide may be useful for labeling glioblastomas in general. The SBK4 peptide labeled both Gli36Δ5 and LN-229 flank tumors to a similar extent as SBK2 but with different off-rate kinetics (FIGS. 7B, 8B). The levels of Gli36Δ5 and LN-229 tumor labeling with SBK2 or SBK4 peptides were significantly different from the scrambled control peptide, as analyzed with an unpaired student t-test. Two other peptides, SBK1 and SBK3, bound the GBM tumors poorly in vivo, with no significant difference from the scrambled control peptide.

Figure 9:
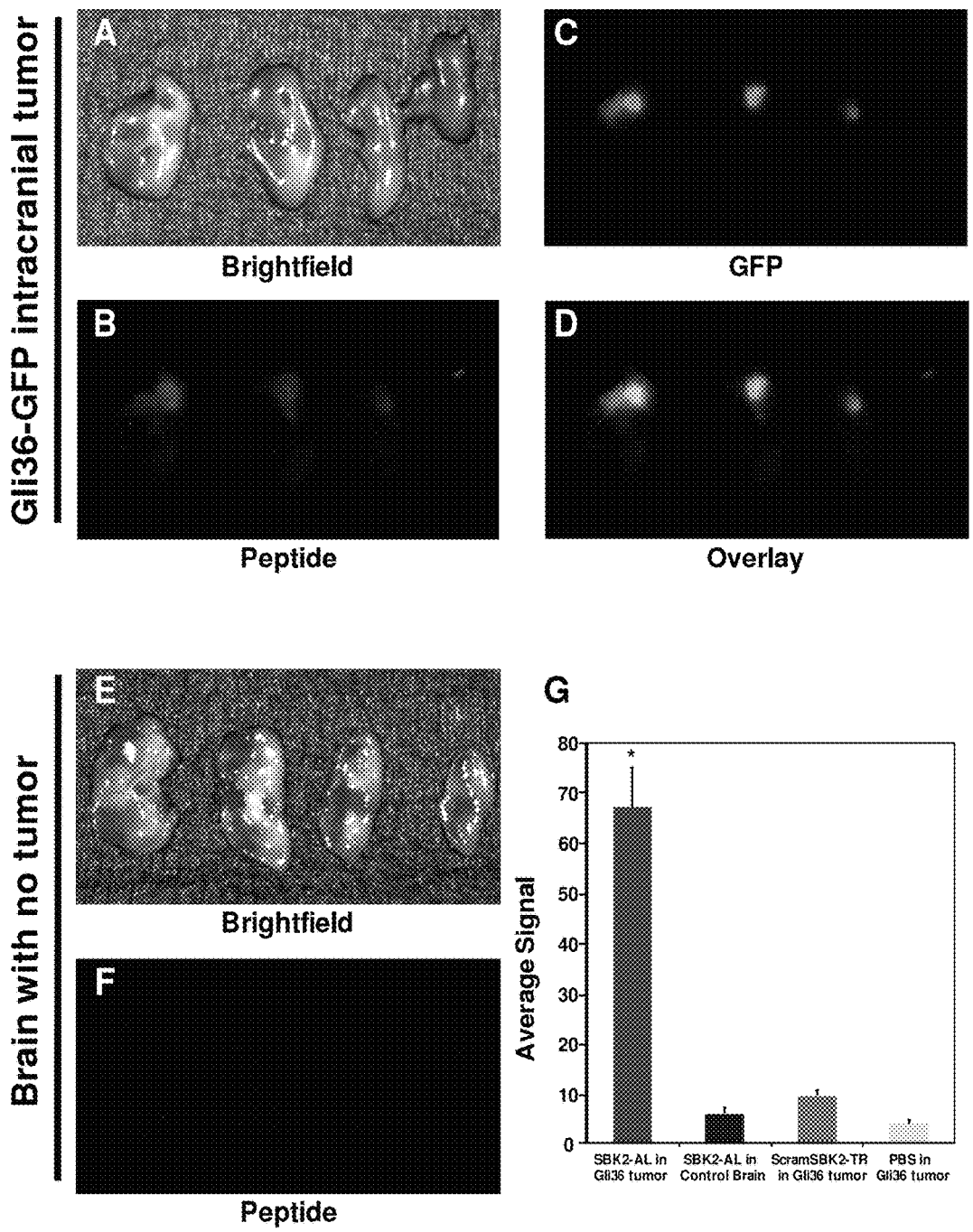
FIG. 9 illustrates PTPµ peptide SBK2 (SEQ ID NO: 5) labels Gli36Δ5 intracranial tumors in vivo. Texas Red (TR) or Alexa (AL)-conjugated PTPµ peptides were administered intravenously to mice with xenograft intracranial tumors of Gli36Δ5 cells. (A) Bright field images of brain slices containing Gli36Δ5-GFP tumor. (C) GFP fluorescence of the slices shown in (A), indicating the location of the Gli36Δ5-GFP tumor in each slice. (B) Alexa-750 fluorescence images of the slices shown in (A), indicating binding of the PTPµ peptide SBK2 (SEQ ID NO: 5). Furthermore, these data suggest that SBK2 crosses the blood brain barrier to detect the glioma cells. (D) Fluorescence overlay image showing both GFP and Alexa-750 fluorescence signals. (E) Bright field image of brain slices from a control brain following tail vein injection of SBK2-AL peptide. (F) Alexa-750 fluorescence image of the slices shown in (E), indicating that SBK2-AL peptide does not bind non-tumor brain. (G) Fluorescence quantitation of peptide binding in brain slices containing Gli36Δ5-GFP tumor cells labeled with SBK2-AL peptide (n=6), scrambled SBK2-AL peptide (n=7), or PBS (n=6). Quantitation of SBK2-AL labeling of control brain slices (n=4) is also shown.

The flank tumor labeling results provided proof of principle that the PTPμ peptides were capable of labeling GBM tumors in vivo. However, it was important to determine whether these peptides could cross the blood brain barrier to reach physiological targets. Athymic nude mice implanted with Gli36Δ5-GFP intracranial tumors were used for PTPμ peptide labeling experiments. SBK2-AL peptide was injected via tail vein and circulated in the mouse for 25 minutes to allow binding to the glioma brain tumor and initial clearance from non-tumor tissue. The Maestro™ FLEX In-Vivo Imaging System cannot image through the skull. Therefore, the animals were sacrificed and the treated brain was removed, sectioned into 1 mm coronal slices and analyzed using the Maestro™ System as described above using filters appropriate for GFP and Alexa-750 fluorescence (FIG. 9). The location of the tumor in each slice is indicated by GFP fluorescence (FIG. 9C). SBK2-AL peptide crossed the blood brain bather and remained bound to the glioma tumor (FIG. 9B). Note the high concentration of peptide binding in the region including and directly adjacent to the Gli36Δ5 tumor (overlay image, FIG. 9D). These results show that the 55 kDa PTPμ fragment secreted by the tumor cells remains highly concentrated in the tissues surrounding the glioma tumor cells, as indicated by the overlap in fluorescence. Furthermore, the SBK2-AL was more effective in detecting small clusters of tumor cells than the GFP signal (FIGS. 9B and 9D section on the far right). SBK2-AL did not bind non-tumor brain (FIG. 9F). Quantitation of brain slice labeling in slices containing Gli36Δ5-GFP cells showed the SBK2-AL peptide labeled tumor cells at a significantly higher level than either scrambled SBK2-TR or PBS control injections (FIG. 9G). Together, these studies show that PTPμ peptide probes SBK2 and SBK4 are useful as reagents to specifically label human glioblastoma tumors non-invasively in vivo.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of detecting cancer cells in a subject comprising:
    administering to a subject a molecular probe that includes a targeting agent that binds to proteolytically cleaved extracellular fragments of receptor protein tyrosine phosphatase (RPTP) cell adhesion molecules expressed in a cancer cell microenvironment in the subject; and
    detecting whether cancer cells are present in the subject by detecting binding of the molecular probe to the proteolytically cleaved extracellular fragment of the cell adhesion molecule, wherein binding of the molecular probe to the proteolytically cleaved extracellular fragment is indicative of cancer cells in the subject.

2. The method of claim 1, further comprising detecting in the subject the molecular probe bound to the proteolytically cleaved extracellular fragment of the cell adhesion molecule to determine cancer cell migration, dispersal, and/or invasion in the subject.

3. The method of claim 1, the RPTP cell adhesion molecule comprising PTPµ.

4. The method of claim 1, the cancer cell comprising a glioma.

5. The method of claim 1, the targeting agent comprising a peptide that specifically binds to SEQ ID NO: 2.

6. The method of claim 5, the targeting agent homophilically binding to SEQ ID NO: 2.

7. The method of claim 3, the targeting agent being a peptide having an amino acid sequence selected from the group consisting of SEQ ID NO: 4, SEQ ID NO: 5, SEQ ID NO: 6, and SEQ ID NO: 7.

8. The method of claim 1, the targeting agent comprising an antibody or fragment thereof that binds to the proteolytically cleaved extracellular fragments of RPTP cell adhesion molecules.

9. The method of claim 8, the antibody or fragment thereof specifically binding to SEQ ID NO: 2.

10. The method of claim 1, the molecular probe further comprising at least one detectable moiety, the detectable moiety comprising at least one of a isotopic label, radiolabel, metal label, or fluorescent dye.

11. The method of claim 1, the molecular probe administered to the subject defining a tumor margin of the cancer cells in the subject.

12. The method of claim 1, the molecular probe being administered parenterally to the subject.

13. The method of claim 1, further comprising administering a cancer therapeutic to the subject after detection of the cancer cells.

14. The method of claim 1, wherein the molecular probe is administered pre-operative a surgical resection of cancer in the subject.

15. The method of claim 1, wherein the molecular probe is administered post-operative a surgical resection of cancer in the subject.

16. A method of treating cancer in a subject comprising:
    administering to a subject a molecular probe that includes a targeting agent that binds to proteolytically cleaved extracellular fragments of receptor protein tyrosine phosphatase (RPTP) cell adhesion molecules expressed in a cancer cell microenvironment in the subject;
    detecting whether cancer cells are present in the subject by detecting binding of the molecular probe to the proteolytically cleaved extracellular fragment of the cell adhesion molecule, wherein binding of the molecular probe to the proteolytically cleaved extracellular fragment is indicative of the location and/or distribution of the cancer cells in the subject; and
    administering a cancer therapeutic to the subject and/or surgically resecting the cancer cells after detection of the cancer cells.

* * * * *